United States Patent
Brunson et al.

(10) Patent No.: US 10,274,369 B2
(45) Date of Patent: Apr. 30, 2019

(54) SYSTEMS AND METHODS FOR AN ABSORBANCE DETECTOR WITH OPTICAL REFERENCE

(71) Applicant: Phoseon Technology, Inc., Hillsboro, OR (US)

(72) Inventors: Lowell Brunson, Hillsboro, OR (US); John Christopher Freitag, Lake Oswego, OR (US); Theresa Thompson, West Linn, OR (US)

(73) Assignee: Phoseon Technology, Inc., Hillsboro, OR (US)

( * ) Notice: Subject to any disclaimer, the term of this patent is extended or adjusted under 35 U.S.C. 154(b) by 0 days.

(21) Appl. No.: 15/650,746

(22) Filed: Jul. 14, 2017

(65) Prior Publication Data
US 2019/0017872 A1    Jan. 17, 2019

(51) Int. Cl.
| | |
|---|---|
| *G01J 3/42* | (2006.01) |
| *G01J 3/28* | (2006.01) |
| *G01J 3/10* | (2006.01) |
| *G02B 27/10* | (2006.01) |
| *G02B 27/14* | (2006.01) |
| *G02B 5/28* | (2006.01) |

(52) U.S. Cl.
CPC . *G01J 3/42* (2013.01); *G01J 3/10* (2013.01); *G01J 3/2803* (2013.01); *G02B 5/283* (2013.01); *G02B 27/1006* (2013.01); *G02B 27/14* (2013.01); *G01J 2003/102* (2013.01); *G01J 2003/425* (2013.01)

(58) Field of Classification Search
CPC ...... G01J 3/10; G01J 3/2803; G01J 2003/102; G01J 2003/425; G02B 27/14; G02B 5/283; G02B 27/1006

USPC .................................................. 356/436–437
See application file for complete search history.

(56) References Cited

U.S. PATENT DOCUMENTS

| 6,127,690 A | 10/2000 | Kitaoka |
| 7,920,265 B1 * | 4/2011 | George ............. G01N 21/1717 |
| | | 324/754.21 |

(Continued)

FOREIGN PATENT DOCUMENTS

| EP | 0886136 A1 | 12/1998 |
| EP | 3088863 A1 | 11/2016 |
| WO | 2007062800 A1 | 6/2007 |

OTHER PUBLICATIONS

"Standard Practice for Testing Fixed-Wavelength Photometric Detectors Used in Liquid Chromatography," ASTM International, Book of Standards vol. 03.06, Jan. 13, 2013, 7 pages.

(Continued)

*Primary Examiner* — Isiaka O Akanbi
(74) *Attorney, Agent, or Firm* — McCoy Russell LLP

(57) ABSTRACT

Systems and methods are provided for a UV-VIS spectrophotometer, such as a UV-VIS detector unit included in a high-performance liquid chromatography system. In one example, a system for the UV-VIS detector unit may include a first light source, a signal detector, a flow path positioned intermediate the first light source and the signal detector, a second light source, and a reference detector. The first light source, the signal detector, and the flow path may be aligned along a first axis, and the second light source and the reference detector may be aligned along a second axis, different than the first axis.

20 Claims, 28 Drawing Sheets

(56) References Cited

U.S. PATENT DOCUMENTS

| | | | |
|---|---|---|---|
| 8,873,061 B1* | 10/2014 | Wells | G01N 21/39 |
| | | | 356/437 |
| 9,322,772 B2* | 4/2016 | Ehring | G01N 30/74 |
| 9,746,430 B2* | 8/2017 | Kim | G01N 21/956 |
| 2003/0025909 A1* | 2/2003 | Hallstadius | A23L 3/003 |
| | | | 356/436 |
| 2012/0196356 A1 | 8/2012 | Wagner et al. | |
| 2013/0016348 A1 | 1/2013 | Ashmead et al. | |
| 2014/0191117 A1 | 7/2014 | Bland et al. | |
| 2015/0153272 A1* | 6/2015 | Ehring | G01N 30/74 |
| | | | 250/373 |
| 2015/0330995 A1 | 11/2015 | Kas | |
| 2016/0320295 A1* | 11/2016 | Smith | G01J 3/10 |

OTHER PUBLICATIONS

ISA Korean Intellectual Property Office, International Search Report and Written Opinion Issued in Application No. PCT/US2018/036732, dated Sep. 20, 2018, WIPO, 17 pages.

\* cited by examiner

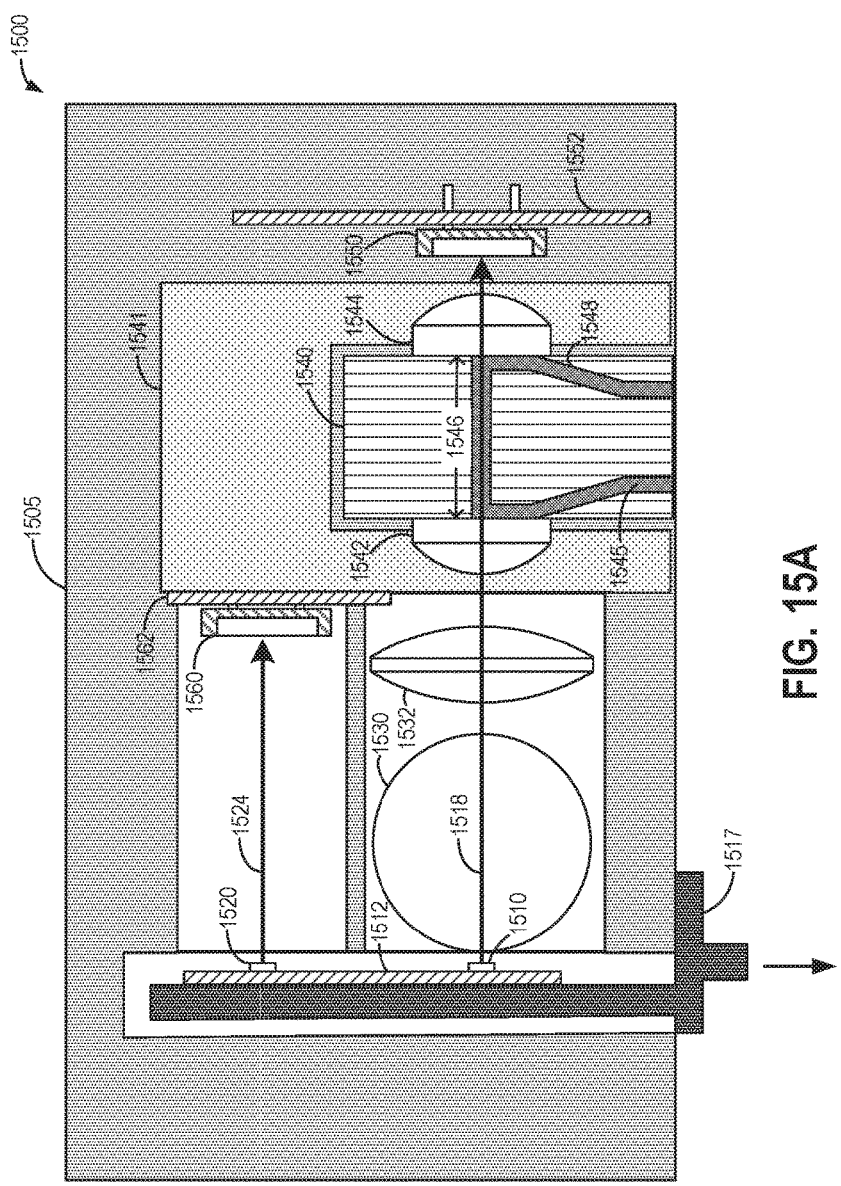

SYSTEMS AND METHODS FOR AN ABSORBANCE DETECTOR WITH OPTICAL REFERENCE

BACKGROUND/SUMMARY

Spectrophotometers quantitatively measure the light reflection or transmission properties of a material as a function of wavelength. UV-VIS spectrophotometers, which utilize light in the ultraviolet WV) and visible (VIS) regions of the electromagnetic spectrum, are commonly used to detect and identify analytes in liquid samples. For example, UV-VIS spectrophotometers may be included as detectors in liquid chromatography systems, such as high-performance liquid chromatography (HPLC), two-dimensional chromatography, ion chromatography, and ultra-high pressure liquid chromatography (UHPLC) systems. An HPLC system may use one or more pumps to flow a pressurized liquid solvent (also termed "mobile phase") containing a sample mixture through a column filled with a solid adsorbent material (also termed "solid phase"). Each component (e.g., analyte) in the sample mixture interacts with mobile phase and the solid phase differently based on their chemical compositions and structures; components with a higher affinity for the mobile phase will flow through the column more quickly, whereas components with a higher affinity for the solid phase will flow through the column more slowly. The different flow rates of the different components enable components of a complex mixture to be purified, for example. In another example, a specific component may be identified based on an amount of time it remains on the column (e.g., retention time). After each component is eluted from the column, the respective component may flow through the detector (e.g., UV-VIS spectrophotometer).

However, the inventors herein have recognized issues with the above configurations. In order to accurately determine the amount of light absorbed by a sample, stray light as well as light intensity fluctuations are accounted for via a reference signal obtained by a reference detector. In the above configurations, a beamsplitter is typically present to divert a portion of the light emitted by the light source to a reference detector. However, such a configuration increases the optical train of the system, increasing cost and size of the system. Further, diverting a portion of the light beam away from the sample may reduce sample absorbance measurement sensitivity.

The inventors herein have recognized the above-mentioned issues and have engineered a way to at least partially address them. In one example, the issues described above may be addressed by a system including a first light source, a signal detector, a flow path positioned intermediate the first light source and the signal detector, a second light source, and a reference detector. The first light source, the signal detector, and the flow path are aligned along a first axis, and the second light source and the reference detector are aligned along a second axis, different than the first axis. In this way, a second light source may be provided as a reference light source, thus allowing substantially all of the light from the primary light source to be directed to the sample. Further, reliance on a beamsplitter may be reduced or eliminated, at least for the purposes of providing a reference light source. The first light source and second light source may be electrically coupled in series, be cooled by the same thermal control device, and/or otherwise be matched so that intensity fluctuations experienced by the first light source are also experienced by the second light source.

The above advantages and other advantages, and features of the present description will be readily apparent from the following detailed description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE FIGURES

FIGS. 15A and 15B depict an embodiment of a UV-VIS detector unit comprising a modular light source.

DETAILED DESCRIPTION

The present description is related to a UV-VIS detector unit. The UV-VIS detector unit may be included in an HPLC system, such as the example HPLC system schematically shown in FIG. 1. Example UV-VIS detector unit embodiments are shown in FIGS. 2-5 and FIGS. 7-16. Specifically, the example embodiments of FIGS. 2-5 and FIG. 16 include a single light source, which may illuminate a sample and also provide its own reference beam. The example embodiments of FIGS. 7-15B include a second light source for providing the reference beam for the first light source. As an example, FIG. 6A illustrates an arrangement of the first light source and the second light source on a common substrate. In the arrangement of FIG. 6A, the first and second light sources may be electrically coupled in series, such as according to the example circuit diagram of FIG. 6B.

Figure 16:
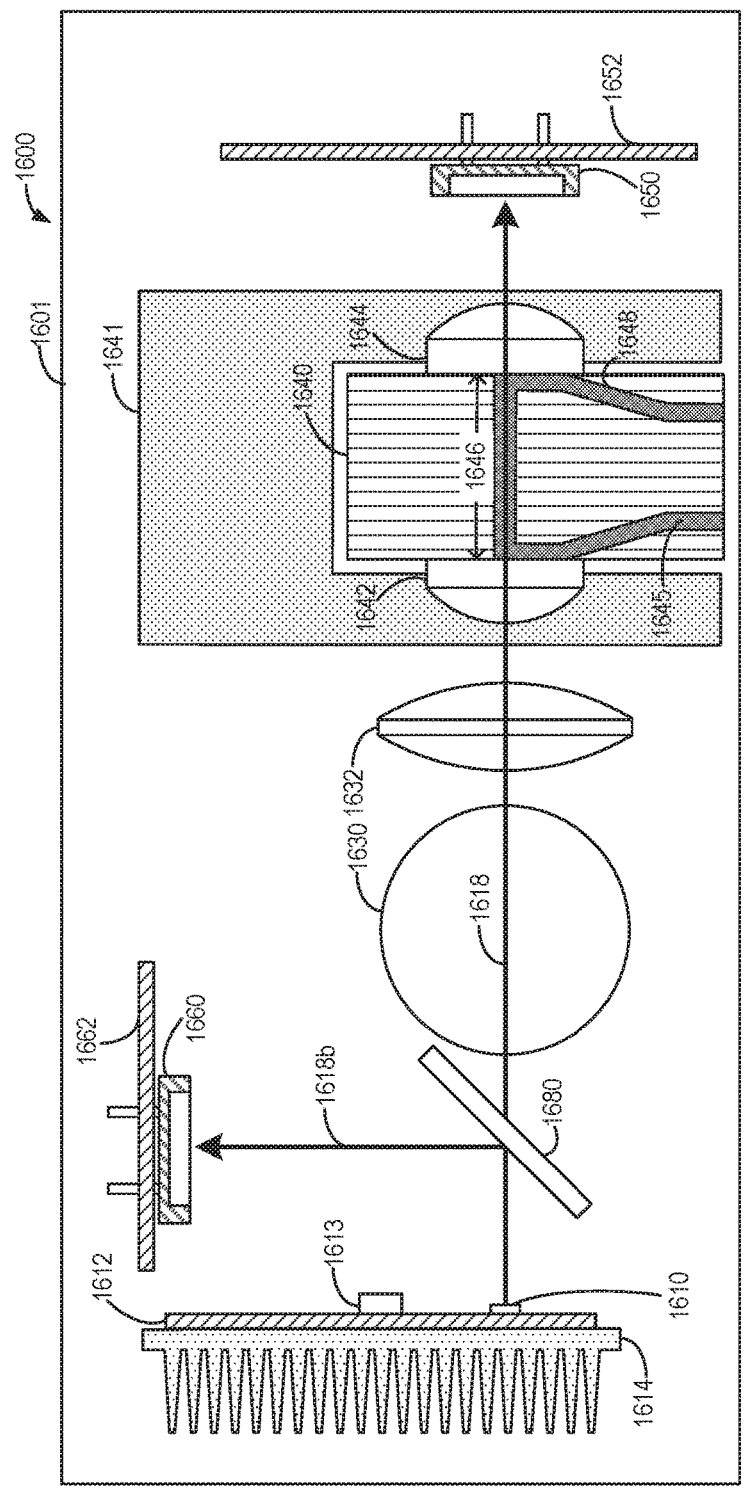
FIG. 16 shows an embodiment of a UV-VIS detector unit that includes a beam splitter between a light source and a flow cell for directing a portion of light from the light source to a reference detector.
Figure 17:
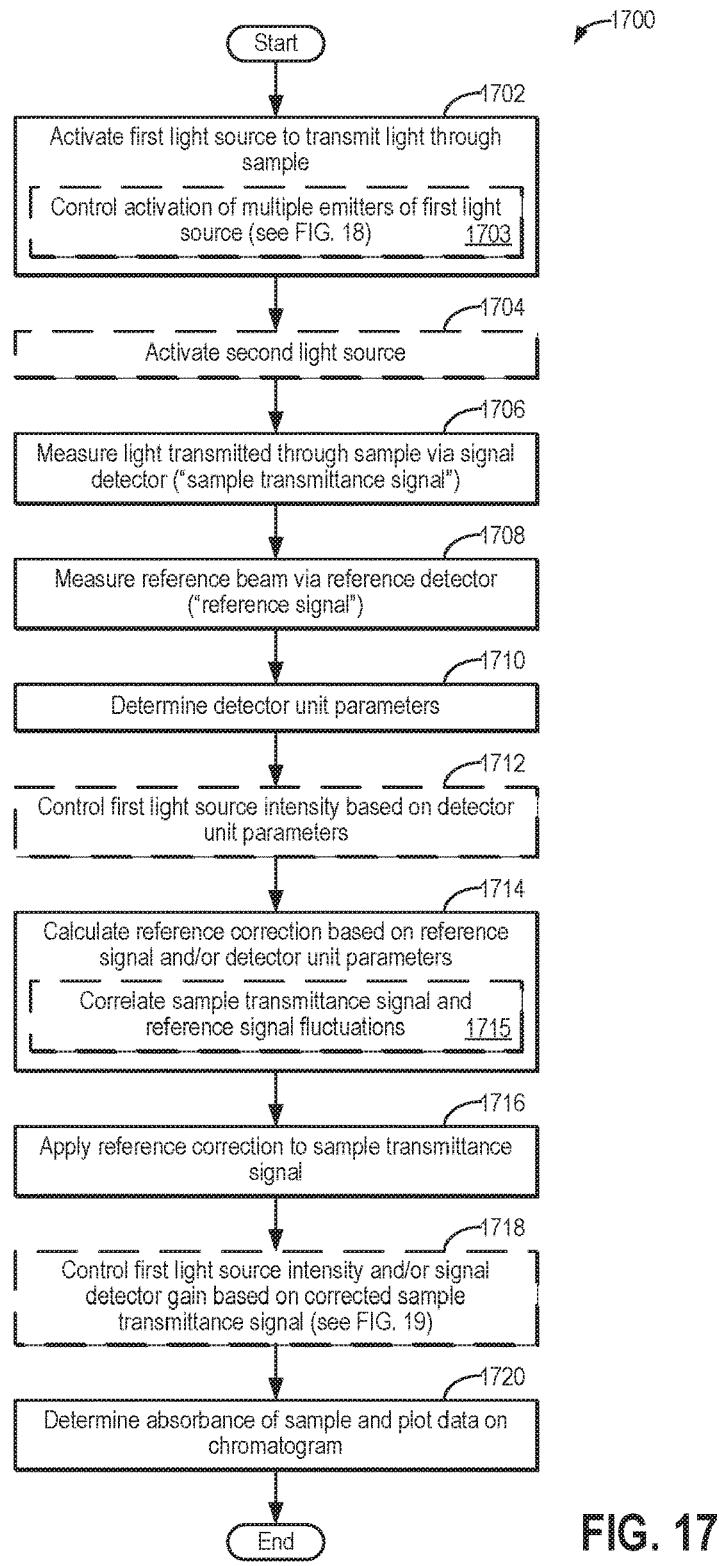
FIG. 17 is a high-level flow chart of an example method for determining sample absorbance using a UV-VIS detector unit.

Each of the example UV-VIS detector units shown in FIGS. 2-5 and FIGS. 7-16 may be used to measure an absorbance of a sample, such as according to the example method of FIG. 17. The resulting absorbance of the sample may be plotted on a chromatogram, such as the example chromatogram shown in FIG. 29. In measuring the absorbance of the sample, activation of each light source may be optimized based on operating parameters of the light source, such as temperature, voltage, and current, example relationships of which are shown in FIG. 23 and FIGS. 25-28. Furthermore, multiple emitters of the light source may be controlled using the example method of FIG. 18. Additionally or alternatively, a ratiometric amplifier, such as the example ratiometric amplifier schematically shown in FIG. 30, may be used to adjust one or more parameters of the UV-VIS detector unit.

Figure 19:
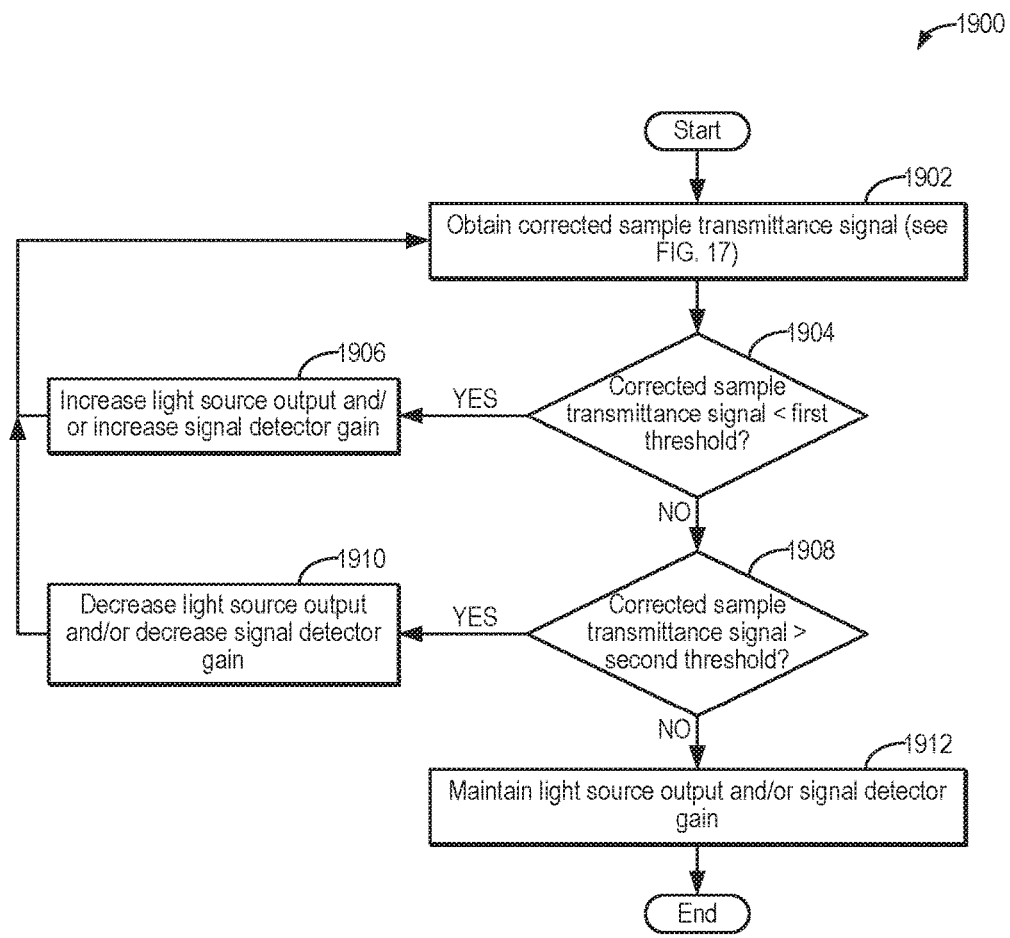
FIG. 19 depicts an example method for extending a dynamic range of a UV-VIS detector unit by adjusting light source intensity and/or detector gain.
Figure 20:
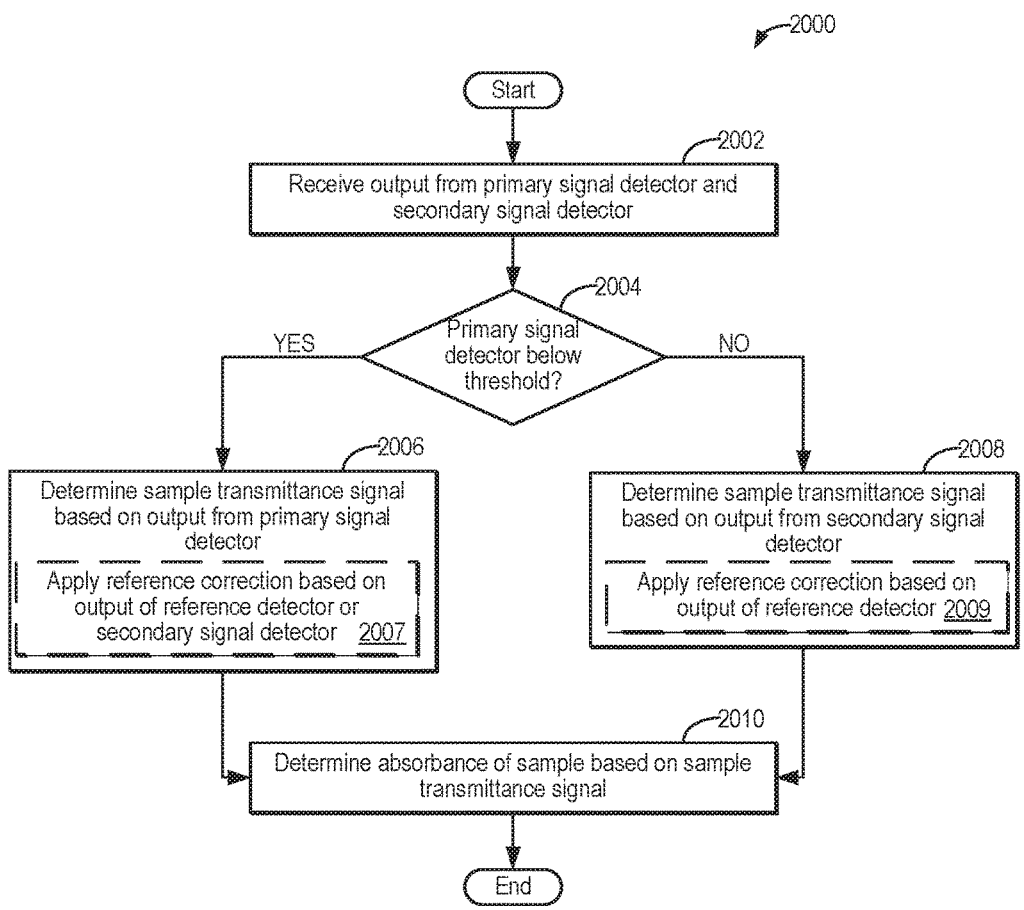
FIG. 20 shows an example method for extending a detection range of a UV-VIS detector unit by using sample back-reflectance as a sample measurement mode.

A controller of the UV-VIS detector unit may utilize the example methods of FIGS. 19 and 20 to extend the dynamic range of concentrations of sample detectable by the detector unit. For example, using the example method of FIG. 19, a detector response curve may be shifted by increasing an intensity of the light source illuminating the sample in order to detect higher concentrations of sample, as illustrated in the example graph of FIG. 24. In another example, back-reflectance of the sample may be used to measure the sample absorbance in order to detect lower concentrations of sample, such as according to the example method of FIG. 20. Further, in some examples, both sample absorbance and fluorescence measurements may be obtained, either simultaneously (such as according to the example method of FIG. 21) or synchronously (such as according to the example method of FIG. 22).

Figure 1:
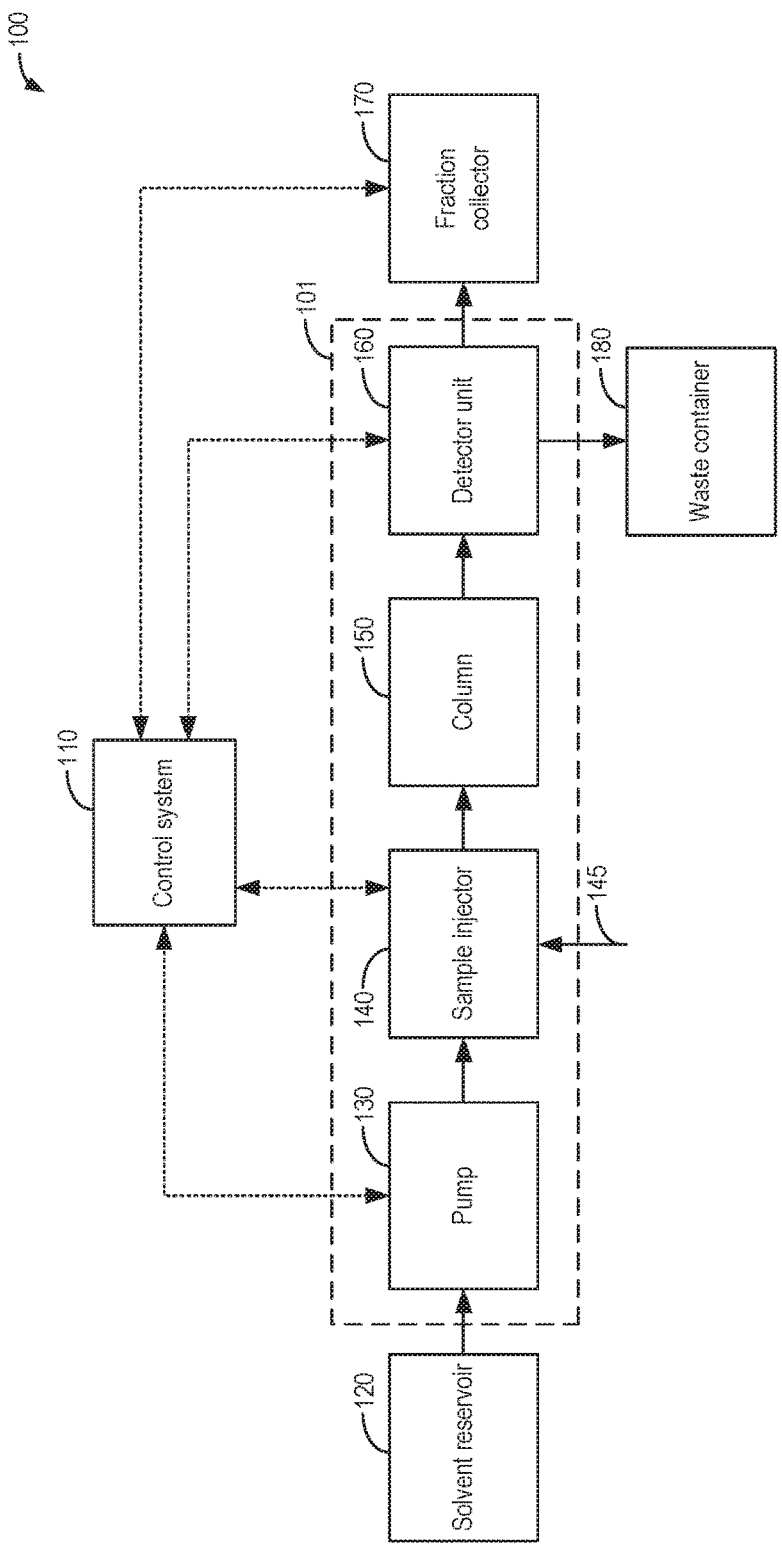
FIG. 1 shows a schematic depiction of a high-performance liquid chromatography (HPLC) system.

Referring to FIG. 1, a schematic diagram of an example HPLC system 100 is shown. HPLC system 100 includes a control system 110, a solvent reservoir 120, a pump 130, a sample injector 140, a column 150, a detector unit 160, a fraction collector 170, and a waste container 180. Multiple components of the HPLC system 100 may be included in a common housing 101. As shown in FIG. 1, the pump 130, sample injector 140, column 150, and detector unit 160 are all housed within common housing 101. However, in other examples, more or fewer components could be housed in the common housing. For example, the solvent reservoir, fraction collector, and/or waste container may be housed in the common housing. Additionally or alternatively, the control system 110 may be housed in the common housing.

The control system 110 is communicatively coupled to other components of the HPLC system (as indicated by dashed lines), as described further below, in order to send and receive signals during system operation. Control system 110 may include a controller, such as a desktop or laptop computer, one or more user input devices (e.g., a mouse, keyboard, touch screen), a display system, and/or a communication system operable to couple the controller to one or more remote computing devices, for example. Control system 110 may receive input from an HPLC system operator to initiate a sample run. In other examples, the sample run may be automated or semi-automated, with control system 110 initiating the sample run according to one or more methods stored in a memory of the control system. The controller of the control system 110 may be an electronic controller and may include a memory storing instructions executable to carry out one or more of the methods described herein. The controller may include one or more physical logic devices, such as one or more processors, configured to execute instructions. Additionally or alternatively, the controller may include hardware or firmware configured to carry out hardware or firmware instructions. The memory may include removable and/or built-in devices, including optical memory, semiconductor memory, and/or magnetic memory.

The memory may include volatile, nonvolatile, dynamic, static, read/write, read-only, random-access, sequential-access, location-addressable, file-addressable, and/or content-addressable devices. The memory and logic device(s) may be integrated together into one or more hardware-logic components, such as field-programmable gate arrays (FPGAs).

Prior to sample injection, HPLC system 100 may be primed with solvent. Control system 110 may activate pump 130, which draws solvent from solvent reservoir 120 that is fluidically connected to pump 130 and other components of HPLC system 100 downstream of pump 130 by lines. Solvent reservoir 120 may hold one or more solvents, such as hexanes, ethyl acetate, dicholormethane, and methanol, with the solvent(s) pumped by pump 130 input into control system 110 by the HPLC system operator or automatically selected based on a pre-programmed method stored in the memory of control system 110. In one example, one solvent, such as hexanes, may be used to prime HPLC system 100. In another example, two solvents at a selected ratio, such as 4:1 hexanes:ethyl acetate or 9:1 dichloromethane:methanol, may be used. Other suitable solvents may be selected to suit the application chemistry, chromatography method, column type, etc. In still another example, three or more solvents may be used. The solvent(s) and ratio used may be selected (e.g., by the HPLC operator or control system 110) based on the components to be purified. Thus, as used herein, the term "solvent" also includes solvent mixtures. The term solvent refers to the mobile phase eluate exiting the column without analyte.

Solvent pumped by pump 130 flows through sample injector 140 and into column 150. Column 150 may contain a solid phase adsorbent, such as silica gel, alumina, or other functionalized medium, selected based on the components to be purified. The length and diameter of column 150 may also be selected based on the scale of the purification and may be installed by the HPLC system operator prior to activating the pump. After flowing through the column, the solvent flows through detector unit 160, which may be a UV-VIS spectrophotometer, as described further herein, although other types of detector units may additionally or alternatively be used, such as fluorescence detectors, photoionization detectors, charged aerosol detectors, electrical conductivity detectors, electrochemical detectors, mass spectrometers, refractive index detectors, etc. In the example of FIG. 1, detector unit 160 is a UV-VIS spectrophotometer. Detector unit 160 may measure a baseline absorbance value of the solvent. Control system 110 may subsequently subtract this baseline absorbance value from values measured after sample injection. After flowing through detector unit 160, the solvent is flowed to waste container 180.

Once HPLC system 100 is primed (e.g., the column is equilibrated with the appropriate solvent) a sample 145 may be injected into the flow path of solvent pumped by pump 130 via sample injector 140. In some examples, sample injector 140 may be an autosampler programmed to inject a sample according to a pre-determined method executed by control system 110. In another example, the HPLC operator may manually operate sample injector 140.

Once sample 145 is injected, it is loaded (e.g., adsorbed) onto the resin of column 150. Different components of sample 145 may have different affinities for the resin as well as the solvent flowing through the column. Thus, components with higher affinities for the resin will move through the column more slowly, while components with higher affinities for the solvent will move through the column more quickly. For example, if the resin is silica gel and the solvent has a low polarity (such as hexanes or a solvent mixture with a high ratio of hexanes), a more polar component will have stronger interactions with the silica gel and will be retained on the column for a longer duration, and a more nonpolar component will have stronger interactions with the solvent and will be eluted from the column after a shorter duration. Further, the solvent(s) used may be adjusted throughout the sample run, such as by increasing the polarity of the solvent mixture, in what is known as a gradient elution. In other examples, the composition of the solvent may remain constant throughout the sample run in what is known as isocratic elution. Other elution methods may also be used, such stepwise elution or combination elution methods.

After each component of sample 145 is eluted from column 150, it passes through detector unit 160. Detector unit 160 exposes the component to one or more wavelengths of light, as described further herein. As light from a light source of detector unit 160 passes through the component, which is diluted in the solvent, some or all of the light may be absorbed, with the amount of light transmitted through the component measured by detector unit 160. Control system 110 may generate an absorbance profile of the component from data received from detector unit 160. From detector unit 160, each component may flow to fraction collector 170. Fraction collector 170 may fill collection containers, such as vials or test tubes, with eluted components. The containers may be filled to a set volume, with the fraction collector advancing to the next container when the set volume is reached. In another example, the fraction collector may advance to the next container based on the absorbance profile of the component that has passed through the detector. If the absorbance profile changes, control system 110 may trigger fraction collector 170 to advance to the next container, as a change in absorbance profile may indicate a different component. Thus, two components may be kept separate. Filled containers may be referred to as fractions.

Control system 110 may generate a chromatogram with absorbance (as measured by detector unit 160) as the Y-axis plotted against retention time (the time it takes a component to pass through HPLC system 100) and/or fraction number as the X-axis. The chromatogram may contain distinct peaks in absorbance corresponding to each analyte (e.g., component) that has passed through the system. Optimally, the absorbance signal is proportional to the concentration of analyte, and the peaks for each analyte are separated. The HPLC system operator may identify fractions containing a component of interest based on the chromatogram and/or absorbance profiles. Therefore, the ability to identify fractions containing the component of interest may depend on the accuracy and sensitivity of the detector.

Fluctuations in light intensity of the light source of detector unit 160, for example, due to stability variations in power supplied to the light source, thermal variations of the light source, or optical power output variations of the light source, lead to fluctuations in light transmittance through sample 145 that are not due to changes in sample absorptivity. For example, light source fluctuations may be observed as baseline short-term or long-term noise or drift. These intensity fluctuations may obscure changes in light transmittance that are due to components in sample 145, especially at low concentrations. Thus, various configurations may be provided to determine fluctuations in light intensity, which can then be used by the controller of control system 110 to correct the sample measurement.

FIGS. 2-16 show example configurations of components of a UV-VIS detector unit that may be included in an HPLC system, such as detector unit 160 of FIG. 1. Like components of FIGS. 2-16 are numbered similarly and may not be reintroduced. In particular, FIGS. 2-5 illustrate examples of UV-VIS detector units with a single light source that utilize backscattered or reflected light as a reference for determining light source fluctuations. Thus, light emitted by the light source itself may be used to determine intensity fluctuations. Using a single light source to provide both a sample signal a reference signal simplifies the optical train, which may reduce the cost and size of the detector unit. Further, intensity fluctuations in the reference signal will be identical to those in the sample signal, with no additional corrections or correlations needed to account for light source variation. In contrast, FIGS. 6-15B show examples of UV-VIS detector unit configurations that include more than one light source. For example, a first light source may interrogate the sample and a second light source may provide a reference beam. The second light source may be chosen, positioned, and connected in such a way that light intensity variations in the second light source may be correlated to variations of the first light source, as further described with respect to FIG. 17. In particular, the first and second light sources may be matched within an acceptable tolerance, such as matched devices (e.g., LEDs) from the same batch or same sorted bin. In another example, the first and second light sources may not be matched, but may respond in such a way that intensity fluctuations may be correlated. Using a separate light source as the reference has an advantage of isolating the reference beam from possible back-reflectance that could be caused by changes in the sample or attenuation of the source instead of changes in light intensity. Any of the detector unit configurations may include a modular light source for customizability, as described with respect to FIGS. 15A and 15B.

Figure 2:
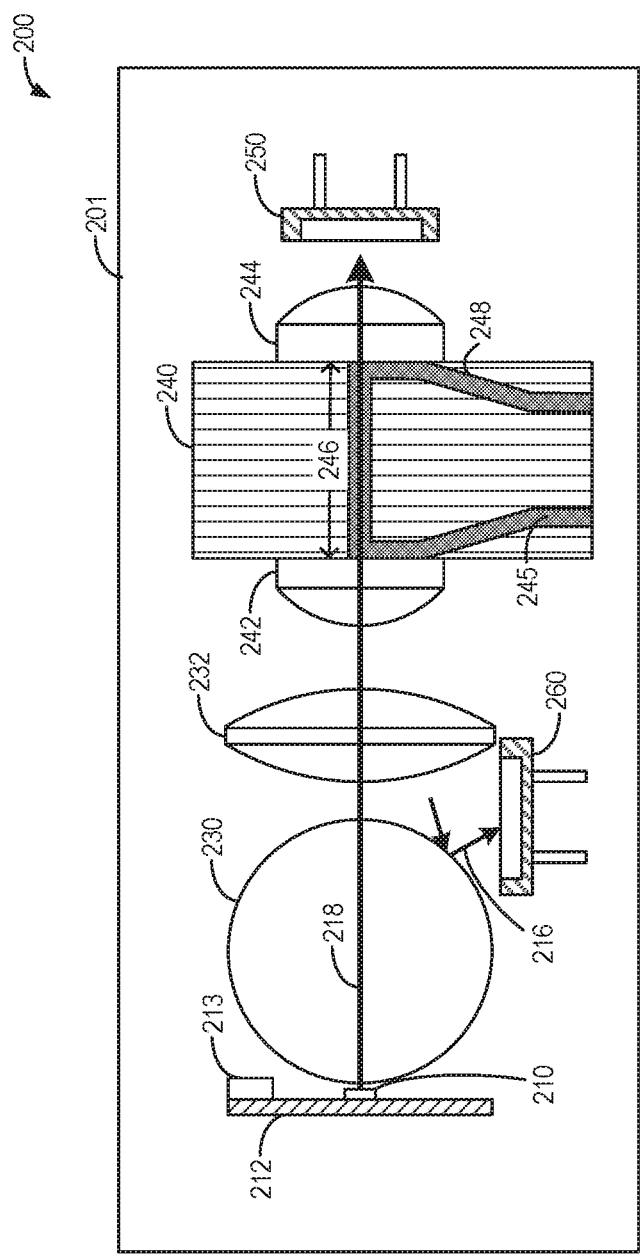
FIG. 2 shows a schematic of a first embodiment of a UV-VIS detector unit that utilizes back-scattered light from a single light source as a reference beam.

FIG. 2 shows a first example configuration of a UV-VIS detector unit 200, which may be included in an HPLC system, such as the HPLC system of FIG. 1. As such, detector unit 200 may be a non-limiting example of detector unit 160 of FIG. 1. However, detector unit 200 may be utilized in other chromatography or spectrophotometry systems without departing from the scope of this disclosure. Detector unit 200 may include a housing 201 that houses a plurality of components of the detector unit, including a light source 210, flow cell 240, signal detector 250, reference detector 260, and optional coupling optics, as explained in more detail below.

Light is emitted from a light source 210, which is coupled (e.g., mounted or bonded) to a substrate 212. Substrate 212 may include a suitable substrate, such as a chip on submount, TO can, C-mount, or butterfly mount. Light source 210 may be a light-emitting diode (LED), organic LED (OLED), laser diode, plasma discharge, or other light source. In one example, light source 210 may be a single emitter that emits light of a single wavelength (or a single wavelength range, such as 620 to 640 nm for an LED that emits red light). In another example, the light emitted by light source 210 may be of variable wavelength, such as a tunable laser diode. In still another example, light source 210 may comprise a plurality of emitters, each emitter of the plurality of emitters emitting light of a single wavelength, such as an array of LEDs (e.g., "multi-color LEDs" or "RGB-LEDs"), or of variable wavelength, such as an array of laser diodes, as further described with respect to FIG. 6A. Further, the plurality of emitters may be packaged together or separately.

A temperature sensor 213 may also be coupled to substrate 212 for determining a temperature of light source 210. Output from temperature sensor 213 may be received by a controller, such as the controller included in control system 110 of FIG. 1, to adjust the intensity of light source 210, as further described with respect to FIG. 17.

The light emitted by light source 210 may travel along a light path 218 to a flow cell 240. In some examples, the light traveling along the light path 218 may pass through coupling optics to focus, redirect, or otherwise condition the light before reaching the flow cell. The coupling optics may include lenses (e.g., ball lens, collimating lens, Fresnel lens) collimators, light guides, and/or other optics. As shown in FIG. 2, the light passes through a first lens (e.g., coupling optic) 230 and then through a second lens 232 before entering the flow cell 240. Flow cell 240 provides a sample interrogation region for taking a measurement of a sample 245. Sample 245 flows through a flow path, such as via a capillary 248, within flow cell 240. For example, if UV-VIS detector unit 200 is included in an HPLC system, sample 245 may flow through flow cell 240 after eluting from an HPLC column (such as column 150 of FIG. 1) and before reaching a fraction collector (e.g., fraction collector 170 of FIG. 1). In the sample interrogation region of the flow path, sample 245 may be exposed to light path 218. As used herein, "flow path" may refer to a region of the flow cell (e.g., defined by a portion of a capillary) configured to flow a sample and also configured to receive and pass light. In other words, the capillary of FIG. 2 may include regions that direct the sample to and from the flow path, but the flow path may only include the portion of the capillary that is positioned to receive light from the light source. Flow cell 240 may be comprised of metals, polymers, ceramics, quartz, and/or glass, etc. In another example, flow cell 240 may be formed between transparent plates that have been bonded together. In the present example, flow cell 240 includes a first lens 242 and a second lens 244 that allow light to enter and exit the flow cell, respectively. In another example, first lens 242 and second lens 244 may be omitted, and light may enter and exit flow cell 240 through transparent windows. After exiting the flow cell, light in light path 218 may reach a signal detector 250.

As shown in the example of FIG. 2, light path 218 is parallel to the direction of sample flow in flow cell 240, making flow cell 240 a longitudinal flow cell with a pathlength 246. The flow path may have a longitudinal axis that is parallel to the light path, for example, and that is parallel to the direction of sample flow in the flow path. In other examples, light path 218 may be perpendicular to the direction of sample flow in flow cell 240 for a transverse flow cell. The longitudinal flow cell configuration allows for a longer pathlength (without increasing the flow cell volume or introducing cross-sectional area changes, which would result in peak broadening) than the transverse flow cell configuration, which enables more interactions to occur between sample 245 and the light in light path 218, increasing sample absorbance, as described further below.

In some examples, light transmitted transversely through the flow path may undergo total internal reflectance at the walls of the flow cell to increase an effective pathlength of light interacting with the sample being analyzed. In this case, the pathlength is not simply the geometric distance between first lens 242 and second lens 244 (e.g., pathlength 246), but a larger value that depends on a difference in refractive index of the sample and the flow cell walls and a mean effective optical pathlength from multiple bounces of scattered beams from the flow cells walls. This effective pathlength may vary depending on slight changes to the samples refractive index, such as when the analyte composition of the sample changes. Therefore, if total internal reflectance is used to increase the effective pathlength of flow cell 240, UV-VIS detector unit 200 may first be calibrated by injecting known concentration gradients of analyte through the HPLC system.

Light source 210, first lens 230, second lens 232, the sample interrogation region of flow cell 240, and signal detector 250 are all positioned along a common axis traversed by light path 218. As light in light path 218 passes through sample 245 within flow cell 240, at least a portion of the light is absorbed by sample 245. Transmitted (e.g., unabsorbed) light exits flow cell 240 through second lens 244 and is detected by signal detector 250, which may be a variable-wavelength detector or a diode array, for example. Signal detector 250 may output a signal (e.g., in volts or amps) that is relative to an optical power or intensity (I) of light transmitted through flow cell 240 (and sample 245) along light path 218. For example, as the intensity of light transmitted through flow cell 240 increases, the voltage output of signal detector 250 increases. The signal output by signal detector 250 may be received by the controller, which may store data from signal detector 250 and perform various data processing actions, as described further herein.

Sample 245 may include one or more analytes diluted in solvent. Thus, the light absorbed by sample 245 includes light absorbed by the one or more analytes and light absorbed by the solvent. A blank correction may be performed in order to account for the absorbance of the solvent and more accurately measure the absorbance of analyte(s) in the sample. In one example, light transmittance (T) through flow cell 240 at a given time t may be determined as: $T=I_{SIG(t)}/I_{SIG\_0}$, where $I_{SIG(t)}$ is the light intensity measured by signal detector 250 at the given time, and $I_{SIG\_0}$ is the light intensity measured by signal detector 250 during a "blank" condition (e.g., pure solvent before sample is added to the HPLC system). During a sample run, the controller may perform the blank correction in real-time (or near real-time) or may perform the blank correction for all time points after the sample run is finished.

Even though light transmittance is measured by signal detector 250, absorbance is more commonly used as a measure of absorption due to the linear relationship between absorbance and concentration defined by the Beer-Lambert law, $A=\varepsilon cl$, where A is the absorbance; $\varepsilon$ is a molar extinction coefficient (e.g., molar absorptivity), which is an intrinsic property of a chemical species; c is the concentration; and l is the pathlength. As may be seen from the Beer-Lambert law, absorbance is directly proportional to pathlength. Thus, as the pathlength of the flow path of the flow cell 240 increases, absorbance increases, which may aid in the detection of low-concentration analytes. Transmittance and absorbance may be related by the equation $A=-\log_{10}(T)$, which may be used by the controller to convert a transmittance signal into a sample absorbance measurement.

In some conditions, the light emitted by the light source may fluctuate (e.g., in intensity and/or wavelength). For example, variations in the current supplied to the light source and/or variations in the temperature of the light source may result in changes to the intensity and/or wavelength output by the light source. Such fluctuations in the light source may result in erroneous sample concentration measurements if not accounted for. Thus, detector units generally include a separate reference detector that measures the light output from the light source that does not pass through the sample. In some examples, a beam splitter may redirect a portion of the light output by the light source to the reference detector. However, the beam splitter may add cost and complexity to the detector unit.

Thus, according to embodiments disclosed herein, the reference detector may be positioned to detect light in the detector unit that has reflected or backscattered off of coupling optics or other structures in the detector unit (e.g., a reflector, walls of flow cell 240, walls of the housing 201 of the detector unit, etc.). As shown in FIG. 2, a portion of light may be reflected or backscattered by sample 245 and/or coupling optics (e.g., lenses) of UV-VIS detector unit 200. In the example of FIG. 2, light 216 that is backscattered by first lens 230 and second lens 232 is measured by a reference detector 260, which is positioned off-axis from the common axis of light source 210, first lens 230, second lens 232, flow cell 240, and signal detector 250. Thus, light 216 may serve as a reference beam. Reference detector 260 may operate similarly to signal detector 250, outputting a voltage relative to an intensity of light detected. The control system may correlate fluctuations in light intensity measured by reference detector 260 with fluctuations in light intensity measured by signal detector 250 to generate a reference correction, as further described with respect to FIG. 17.

Figure 3:
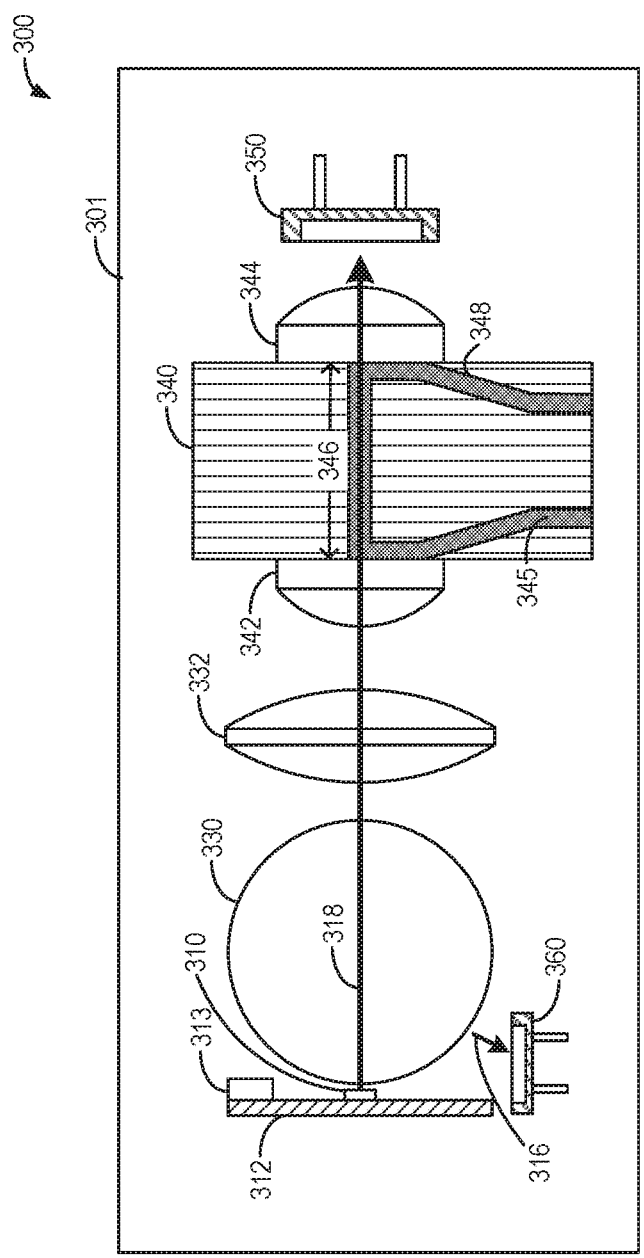
FIG. 3 shows a schematic of a second embodiment of a UV-VIS detector unit that utilizes back-scattered light from a single light source as a reference beam.

In the example of FIG. 2, reference detector 260 is positioned between the first lens 230 and the second lens 232. However, in other examples, the reference detector may be positioned before the first lens. For example, FIG. 3 shows an example HPLC UV-VIS detector unit 300 that, similar to detector unit 200, includes a housing 301; a light source 310 mounted to a substrate 312; a temperature sensor 313 mounted on the substrate; a flow cell 340, including a first lens 342, a second lens 344, and a capillary 348 configured to flow a sample 345 through a sample-interrogating pathlength 346; a signal detector 350; and a reference detector 360. Further, optional coupling optics may be included, such as a first lens 330 and second lens 332, and light source 310 is configured to output light along a light path 318. In detector unit 300, reference detector 360 is positioned between light source 310 and first lens 330, off-axis from the common axis of light source 310, first lens 330, second lens 332, flow cell 340, and signal detector 350. In such a configuration, reference detector 360 may measure light 316 reflected or backscattered by first lens 330.

Figure 4:
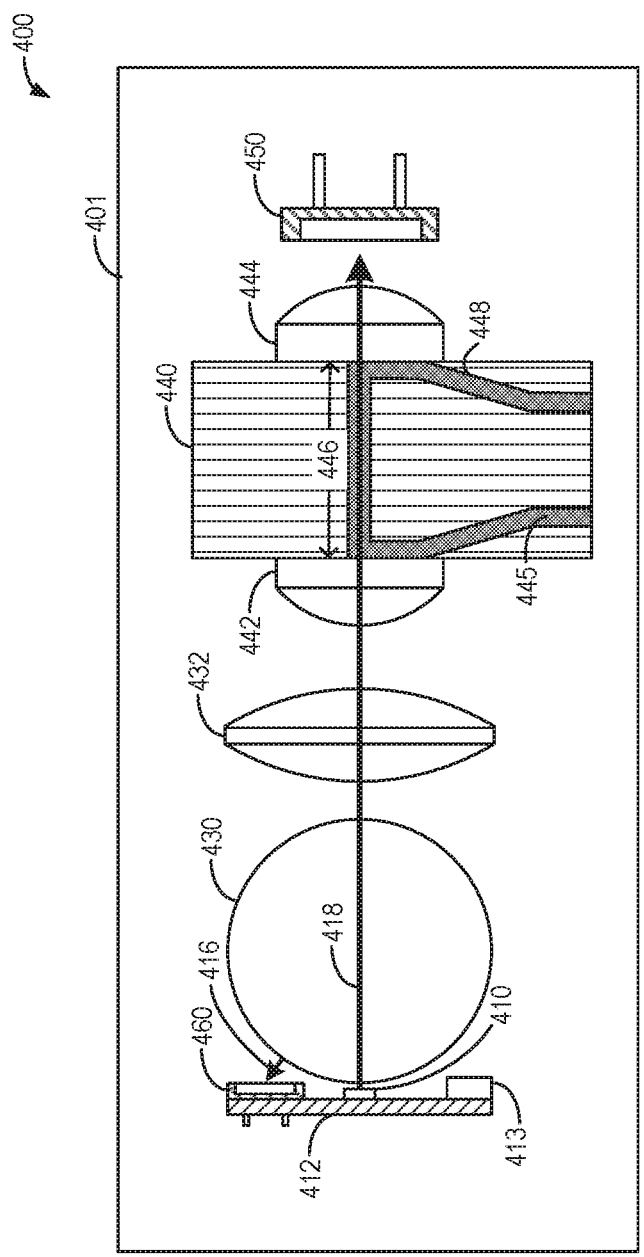
FIG. 4 shows a schematic of a third embodiment of a UV-VIS detector unit that utilizes back-scattered light from a single light source as a reference beam.

In another embodiment, as shown in UV-VIS detector unit 400 of FIG. 4, a detector unit 400 is similar to detector unit 200 and includes a housing 401; a light source 410 mounted to a substrate 412; a temperature sensor 413 mounted on the substrate; a flow cell 440, including a first lens 442, a second lens 444, and a capillary 448 configured to flow a sample 445 through a sample-interrogating pathlength 446; a signal detector 450; and a reference detector 460. Further, optional coupling optics may be included, such as a first lens 430 and a second lens 432, and light source 410 is configured to output light along a light path 418. In detector unit 400, reference detector 460 is coupled to substrate 412 alongside light source 410 and measures light 416 reflected or backscattered by first lens 430, walls of the detector unit housing 401, and/or other components. Thus, by relying on backscattered light as a reference beam, a beam splitter may be dispensed with (at least for the purposes of reference detection), allowing for miniaturization of the detector unit. Additionally, in examples where the detector unit is positioned on the substrate along with the light source, further miniaturization of UV-VIS detector unit 400 may be possible.

Figure 5:
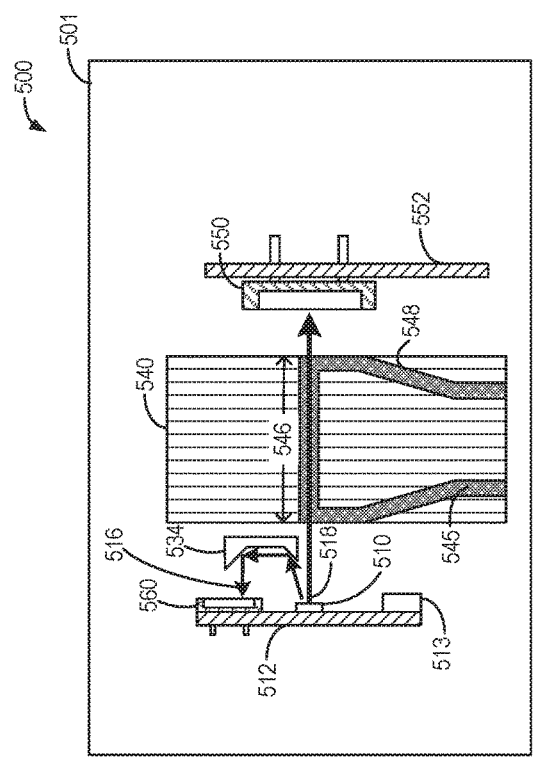
FIG. 5 illustrates an example of a UV-VIS detector unit that includes a reflector to generate a reference beam from a single light source.
Figure 6A:
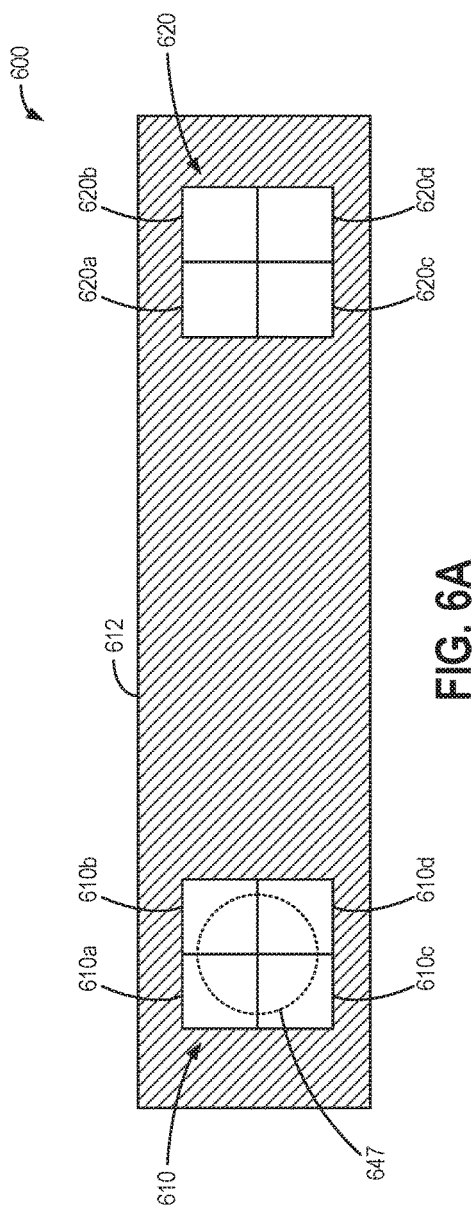
FIG. 6A illustrates an example configuration of a first light source and a second light source coupled to a common substrate, each of the first and second light sources comprising multiple light emitters.

In the example of FIG. 5, UV-VIS detector unit 500 is similar to detector unit 200 and includes a housing 501; a light source 510 mounted to a substrate 512; a temperature sensor 513 mounted on the substrate; a flow cell 540, including a first lens 542, a second lens 544, and a capillary 548 configured to flow a sample 545 through a sample-interrogating pathlength 546; a signal detector 550 coupled to a substrate 552; and a reference detector 560. Light source 510 is configured to output light along a light path 518. In detector unit 500, a reflector 534 is present to pick-off light 516 as the reference beam. Unlike a beam splitter, which directs a portion of on-axis light to a second light path, leaving less light in the primary light path (such as light path 518), reflector 534 may utilize off-axis or stray rays of light that are not coupled through light path 518. In the example of FIG. 5, coupling optics between flow cell 540 and light source 510 are omitted, simplifying the optical train of UV-VIS detector unit 500. In other embodiments, coupling optics may be included, with reflector 534 positioned between light source 510 and the coupling optics. For example, the smaller size of reflector 534 relative to a beam splitter enables the reflector to be positioned immediately adjacent to light source 510. Reference detector 560 is shown coupled to substrate 512 alongside light source 510, as in FIG. 4. However, other configurations of reflector 534 and reference detector 560 may be possible.

As mentioned above, the UV-VIS detector configurations of FIGS. 2-5 enable intensity fluctuations of a light source to be measured directly (e.g., using light from the light source itself). However, other UV-VIS detector configurations are also possible, such as those that utilize a second light source as a reference to determine intensity fluctuations in a first light source configured to illuminate a sample.

FIG. 6A shows an example front view of an arrangement 600 of two light sources coupled to a common substrate 612 that may be included in a UV-VIS detector unit. Further, each light source is shown including a plurality of emitters. A first light source 610 is comprised of four emitters 610a, 610b, 610c, and 610d, placed in a two by two array. A second light source 620 is comprised of four emitters 620a, 620b, 620c, and 620d, placed in a separate two by two array. In other examples, the number and the arrangement of emitters on substrate 612 may vary. For example, a light source may include a single emitter, three emitters arranged in a triangular fashion, nine emitters arranged in a three-by-three array, or other configuration. In another example first light source 610 may comprise a plurality of emitters, and second light source 620 may comprise a single emitter, allowing for fewer devices, lower cost, and miniaturization.

First light source 610 and second light source 620 are both coupled to common substrate 612. Further, first light source 610 and second light source 620 may be electrically connected in series. Further still, first light source 610 and second light source 620 may be coupled to a common thermal device. In other examples, first light source 610 and second light source 620 may be coupled to different substrates or may be thermally regulated separately, as described further below.

Figure 6B:
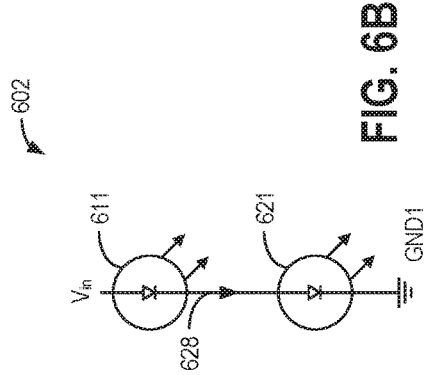
FIG. 6B shows an example circuit diagram of two light sources electrically coupled in series.

An example circuit diagram 602 of an electrical coupling of a first light source 611 and a second light source 621 is shown in FIG. 6B. In the example of FIG. 6B, first light source 611 and second light source 621 are both shown as LEDs. First light source 611 may be coupled to an electrical power source, current source ($I_{in}$), or a voltage source ($V_{in}$). Current 628 may flow through first light source 611 and then to second light source 621 such that the electrical drive current that flows through each of the light sources is the same. Second light source 621 is coupled to a ground (GND1). While not shown in FIG. 6B, various other components may be present in the light source circuit, such as a current-limiting resistor, one or more switches, etc. The series coupling of the two light sources shown in FIG. 6B may apply to any of the multiple light source configurations described herein.

Returning to FIG. 6A, dashed circle 647 indicates how the four emitters of first light source 610 may be aligned with a flow path of a corresponding flow cell in the detector unit. Each emitter is positioned to provide a light beam on-axis with the flow path of the flow cell. Further, the flow cell may serve as a limiting aperture for the light emitted by each emitter of first light source 610. In some examples, emitter 620a may serve as the reference for emitter 610a, emitter 620b may serve as the reference for emitter 610b, emitter 620c may serve as the reference for 610c, and 620d may serve as the reference for 610d. Thus, each emitter of first light source 610 may have a dedicated reference emitter in second light source 620. In other examples, the emitter of second light source 620 may be selected independently of the emitter of first light source 610. For example, the emitter may be selected to match the reference emitter or the signal detector, allowing lower cost detectors and/or emitters to be used, or selected based on a lifetime of the emitter. As an example, the first light source emitter may be selected based on the expected absorption band characteristics of the analyte. However, if the absorption band is unknown, each emitter of the first light source may be turned on and off sequentially to determine the emitter that produces an optimal signal. The emitter of the first light source that produces the optimal signal may be then be selected, followed by a selection of a matched reference emitter of the second light source. In still other examples, second light source 620 may interrogate the sample and first light source 610 may serve as the reference. Additionally, when the flow cell is a multi-pass flow cell, as described with respect to FIG. 14, first light source 610 and second light source 620 may alternate between interrogating the sample and providing the reference. The emitters of each light source may be activated individually, sequentially, or simultaneously, as further described with respect to FIG. 18.

Figure 7:
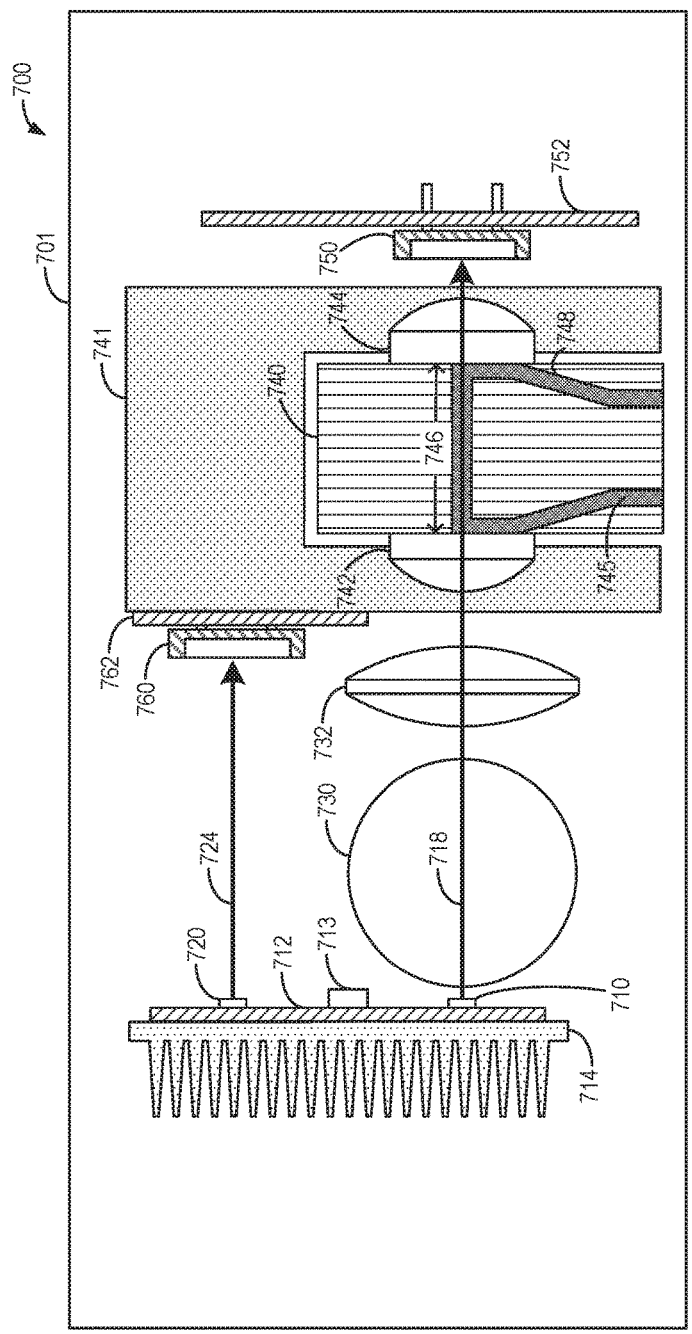
FIG. 7 illustrates a first embodiment of a UV-VIS detector unit that includes a first light source for interrogating a sample and a second light source to provide a reference beam for the first light source.
Figure 8:
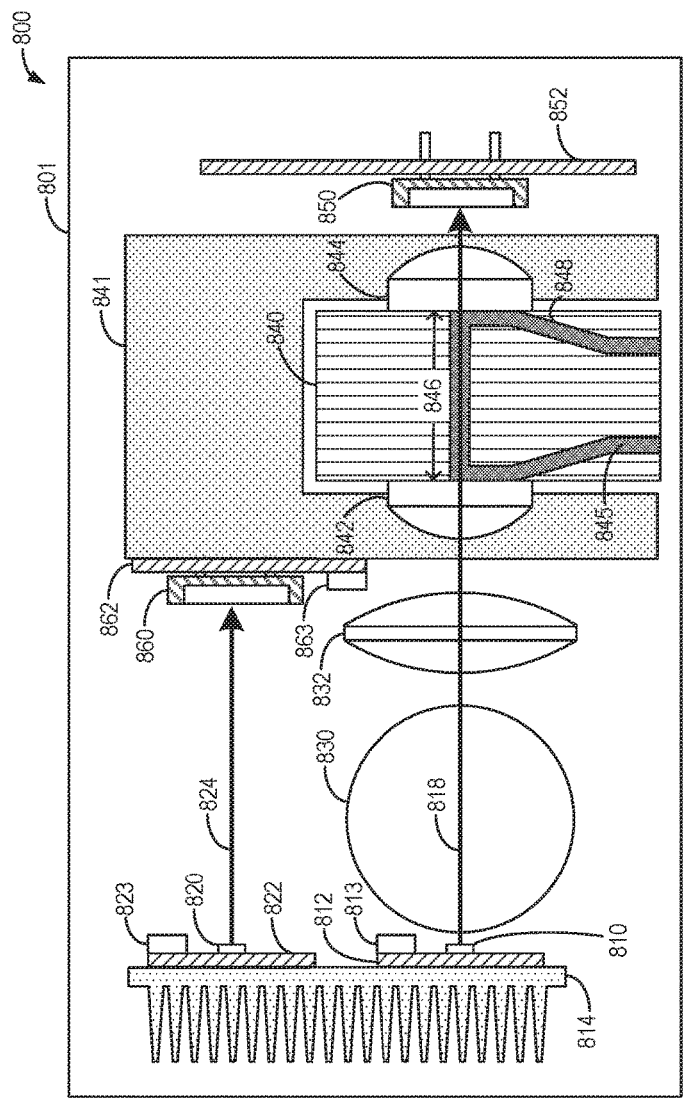
FIG. 8 illustrates a second embodiment of a UV-VIS detector unit that includes a first light source for interrogating a sample and a second light source to provide a reference beam for the first light source.

Turning now to FIG. 7, an example of a UV-VIS detector unit 700 that includes two light sources is shown. UV-VIS detector unit 700 includes a housing 701 housing a first light source 710 for interrogating a sample 745 within a flow cell 740 along a light path 718. The first light source 710, the flow path of the flow cell 740, and a signal detector 750 are aligned along a common axis. Detector unit 700 further includes a second light source 720 for providing a reference beam to a reference detector 760 via a light path 724. The second light source 720 and reference detector 760 are aligned along an axis that is off-axis from the common axis along which the first light source 710, the flow path of the flow cell 740, and signal detector 750 are aligned. As such, light path 724 of second light source 720 is distinct from light path 718 of first light source 710.

In some examples, first light source 710 and second light source 720 may be electrically connected in series. In the example of FIG. 7, first light source 710 and second light source 720 are coupled to a common substrate 712, which is mounted (e.g., clamped or bonded) to a single thermal device 714, making first light source 710 and second light source 720 thermally coupled. Thermal device 714 may be an active thermal regulation system, such as a Peltier device, or may be a passive thermal regulation system, such as a heatsink. A temperature sensor 713 is shown coupled to substrate 712 for measuring a temperature of the substrate. In other examples, the temperature sensor may be positioned to measure a temperature of one of the light sources directly and/or additional temperature sensors may be present. Output from temperature sensor 713 may be used to control thermal device 714, first light source 710, and/or second light source 720, as further described with reference to FIG. 17. However, in other examples, temperature sensor 713 may be omitted or coupled to a different component of the detector unit, such as flow cell 740.

In the configuration depicted in FIG. 7, first light source 710 and second light source 720 may exhibit nearly identical intensity fluctuations since they are electrically coupled (and therefore driven by the same drive current) and experience the same thermal regulation. However, in other examples, the first and second light sources may not be electrically coupled. For example, first light source 710 and second light source 720 may be electrically driven using matched differential amplifiers, and a suitable correlation function may be applied to correlate intensity fluctuations between the two light sources, as further described with reference to FIG. 17.

Similar to the flow cells described previously, flow cell 740 includes a capillary 748 configured to flow sample 745 through a pathlength 746, a first lens 742, and a second lens 744. In the example of FIG. 7, flow cell 740 is shown surrounded by a flow cell housing 741. Flow cell housing 741 provides mechanical structure and optical alignment for components of the UV-VIS detector system. Flow cell housing 741 may include apertures or optically transparent windows for allowing light emitted by first light source 710 and traveling along light path 718 to enter and exit flow cell 740. This may help keep light path 718 isolated from light path 724. As shown in the example of FIG. 7, flow cell 740 is separable from flow cell housing 741, allowing flow cell 740 to be interchanged with other flow cells. In another embodiment, flow cell housing 741 may be directly connected to flow cell 740 in a non-separable fashion, such as permanently bonded or fused. Signal detector 750 is shown coupled to a substrate 752. Reference detector 760 is shown coupled to a substrate 762, which is mounted to flow cell housing 741. Similar to the example detector unit embodiments of FIGS. 2-5, first light source 710 shares a first common axis with first lens 730, second lens 732, the sample interrogation region of flow cell 740, and signal detector 750. Second light source 720 shares a second common axis with reference detector 760, which is different than the first common axis.

Other configurations of the first and second light sources are possible. In the example of UV-VIS detector unit 800 of FIG. 8, which includes a housing 801, a first light source 810 is coupled to a first substrate 812 and a second light source 820 is coupled to a second substrate 822, with both the first and second substrates mounted to the same thermal device 814. A first temperature sensor 813 is shown coupled to first substrate 812, a second temperature sensor 823 is shown coupled to second substrate 822, and a third temperature sensor 863 is shown coupled to substrate 862 of reference detector 860. The output from the first and second temperature sensors may be used by the controller to determine the temperature of the first light source and second light source, respectively. The output intensity of each light source may be controlled based on the respective temperature. Further, the thermal device 814 may be controlled based on each respective temperature. The output from the third temperature sensor may be used by the controller to determine the temperature of the substrate 862. In some examples, if the temperature of the substrate 862 exceeds a temperature limit, auxiliary cooling mechanisms (e.g., fans) may be activated and/or the operator may be notified.

Similar to detector unit 700, detector unit 800 includes a flow cell 840 defined by a housing 841 and including a first lens 842, a second lens 844, and a capillary 848 configured to flow a sample 845 through a sample-interrogating pathlength 846, and a signal detector 850 coupled to substrate 852. Further, optional coupling optics may be included, such as a first lens 830 and a second lens 832, and first light source 810 is configured to output light along a light path 818.

Figure 9:
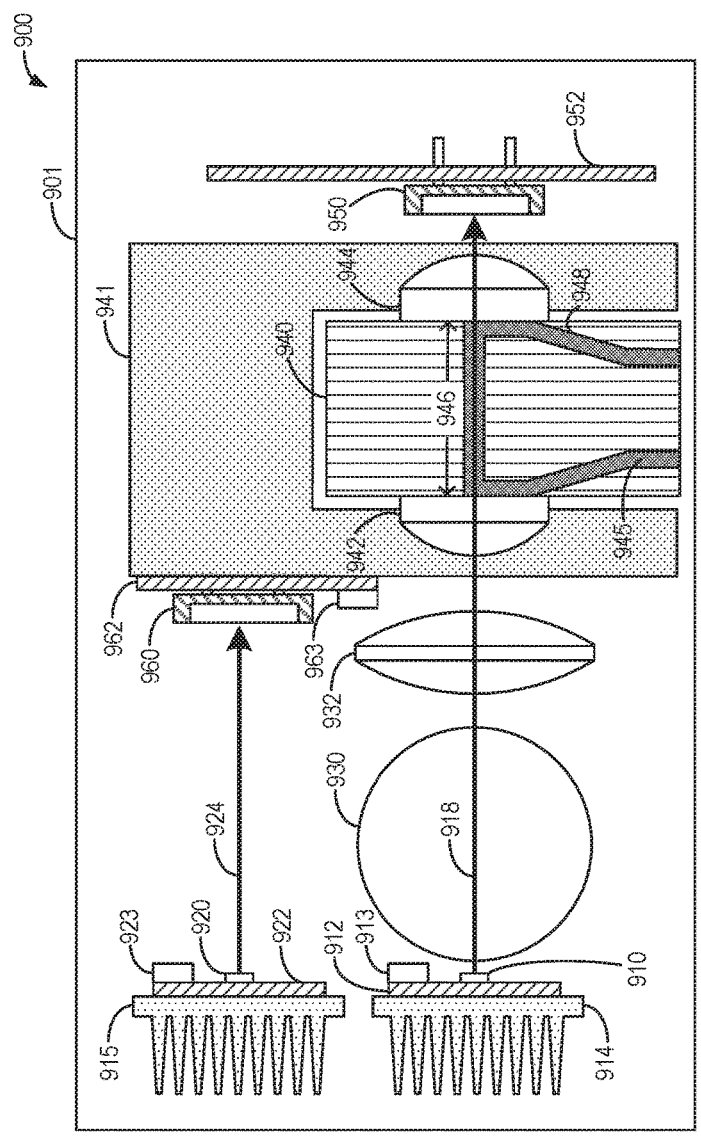
FIG. 9 illustrates a third embodiment of a UV-VIS detector unit that includes a first light source for interrogating a sample and a second light source to provide a reference beam for the first light source.
Figure 10:
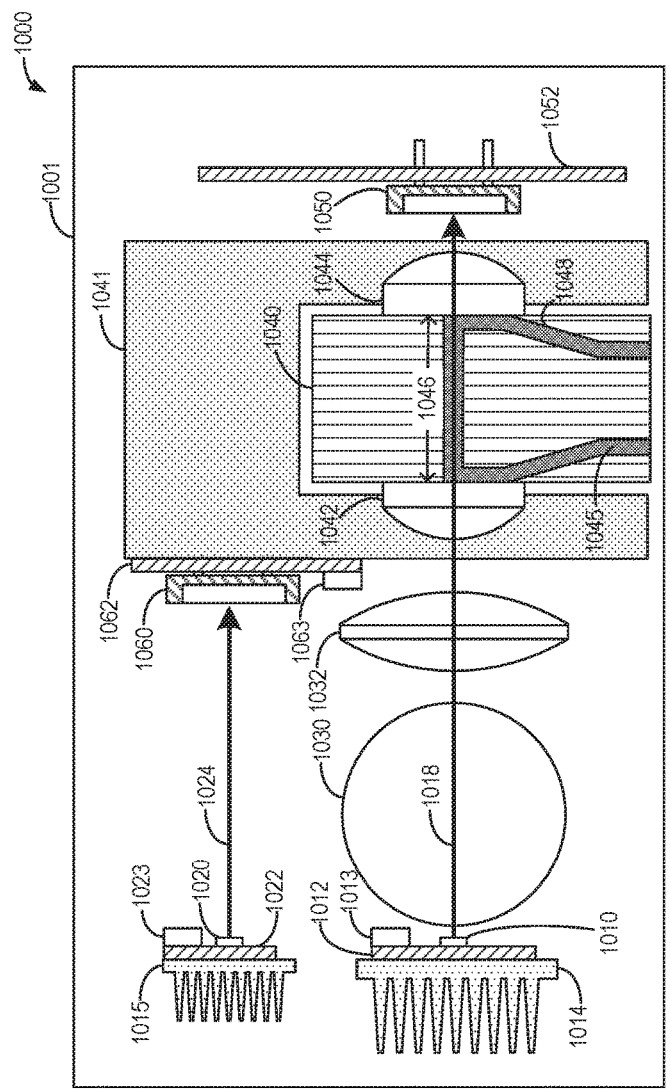
FIG. 10 illustrates a fourth embodiment of a UV-VIS detector unit that includes a first light source for interrogating a sample and a second light source to provide a reference beam for the first light source.

In another example, such as the example of UV-VIS detector unit 900 of FIG. 9, which includes a housing 901, a first light source 910 is coupled to a first substrate 912, which is mounted to a first thermal device 914, and a second light source 920 is coupled to a second substrate 922, which is mounted to a second thermal device 915. In some examples, thermal devices 914 and 915 may each include a temperature sensor coupled thereto. In other examples, such as the example of FIG. 9, a first temperature sensor 913 is coupled to first substrate 912 and a second temperature sensor 923 is coupled to second substrate 922. Separate substrates for first light source 910 and second light source 920 may allow for smaller packaging, design and packaging flexibility, and standardization of parts. Further, thermally regulating each substrate separately may allow compensation for different thermal transient responses, especially during a startup condition prior to thermal equilibrium. For example, first light source 910 may have a thermal time constant and corresponding light output vs. temperature curve, and second light source may 920 have a different thermal time constant and corresponding light output vs. temperature curve. With the light sources coupled to separate thermal devices, a suitable correlation function may be applied to account for differences in the thermal boundary of each light source, for example, as measured by the first and second temperature sensors. For example, when first light source 910 and second light source 920 are operated under the same thermal conditions (even though they are coupled to separate thermal devices), the correlation function compensates for any differences in efficiency (e.g., a slope of optical power vs. LED current) between the two devices, particularly when first light source 910 and second light source 920 are of differing peak wavelengths.

Similar to detector unit 700, detector unit 900 includes a flow cell 940 defined by a housing 941 and including a first lens 942, a second lens 944, and a capillary 948 configured to flow a sample 945 through a sample-interrogating pathlength 946, and a signal detector 950 coupled to a substrate 952. Further, optional coupling optics may be included, such as a first lens 930 and a second lens 932, and first light source 910 is configured to output light along a light path 918.

In the example of FIG. 9, thermal devices 914 and 915 are similar and independent. In other examples, such as the example configuration of UV-VIS detector unit 1000 of FIG. 10, a first thermal device 1014 and a second thermal device 1015 are dissimilar thermal systems. A first light source 1010 is shown coupled to a first substrate 1012, first substrate 1012 coupled to first thermal device 1014, and a second light source is shown coupled to a second substrate 1022, second substrate 1022 coupled to second thermal device 1015. Dissimilar thermal systems may be advantageous when first light source 1010 and second light source 1020 coupled to a second substrate are dissimilar. However, fluctuations in light intensity may still be correlated using a suitable correlation function. For example, if first light source 1010 is higher efficiency and second light source 1020 is lower efficiency, first thermal device 1014 may be a lower performance heatsink and second thermal device 1015 may be a higher performance heatsink, which may help standardize the intensity of light output by the first and second light sources. Further, dissimilar thermal systems may reduce packaging size, reduce cost, simplify manufacturing and assembly, increase standardization of components across multiple product variants, or provide respective thermal time constants (e.g., matched to light source efficiency) to account for differences in emitter efficiencies.

Similar to detector unit 700, detector unit 1000 includes a housing 1001; a flow cell 1040 defined by a housing 1041 and including a first lens 1042, a second lens 1044, and a capillary 1048 configured to flow a sample 1045 through a sample-interrogating pathlength 1046; a signal detector 1050 coupled to a substrate 1052; a reference detector 1060 coupled to a substrate 1062; and temperature sensors coupled to each substrate (e.g., sensors 1013, 1023, and 1063). Further, optional coupling optics may be included, such as a first lens 1030 and a second lens 1032, and first light source 1010 is configured to output light along a light path 1018 while second light source 1020 is configured to output light along a light path 1024, which is off-axis from light path 1018.

Figure 11:
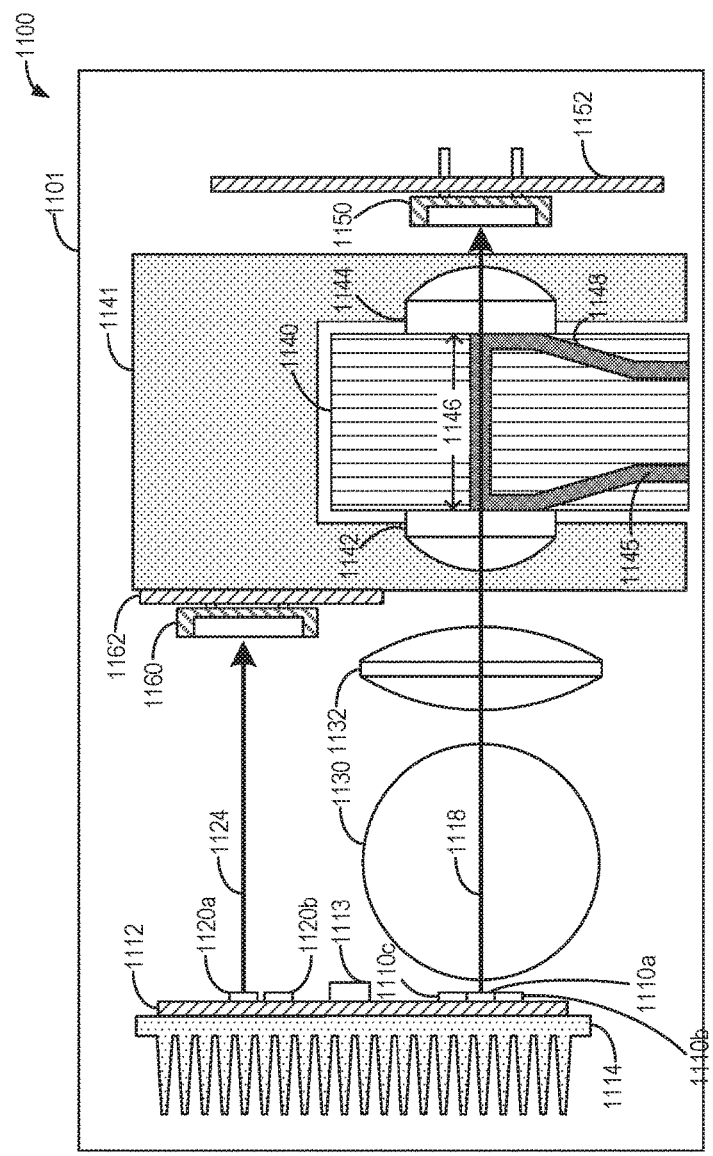
FIG. 11 illustrates a fifth embodiment of a UV-VIS detector unit that includes a first light source for interrogating a sample and a second light source to provide a reference beam for the first light source, each of the first and second light sources including multiple light emitters.

In all of the above described embodiments, the first light source and/or the second light source may each include a plurality of emitters, such as in the example arrangement 600 of FIG. 6A. Another example of this is illustrated in FIG. 11. UV-VIS detector unit 1100 of FIG. 11 is similar to UV-VIS detector unit 700 of FIG. 7 in that a first light source and a second light source are coupled to a single substrate 1112, which is in turn coupled to a single thermal device 1114. In UV-VIS detector unit 1100 of FIG. 11, the first light source includes a first emitter 1110a, shown emitting light in a light path 1118, a second emitter 1110b, and a third emitter 1110c. The second light source includes a first emitter 1120a, shown emitting the light in light path 1124, and a second emitter 1120b. However, a different number of emitters for both the first light source and the second light source may be possible. The emitters in each light source may be activated individually, sequentially, or simultaneously, as further described with reference to FIG. 17.

Similar to detector unit 700, detector unit 1100 includes a flow cell 1140 defined by a housing 1141 and including a first lens 1142, a second lens 1144, and a capillary 1148 configured to flow a sample 1145 through a sample-interrogating pathlength 1146; a signal detector 1150 coupled to a substrate 1152; a reference detector 1160 coupled to a substrate 1162; and temperature sensors coupled to each substrate (e.g., sensor 1113). Further, optional coupling optics may be included, such as a first lens 1130 and a second lens 1132.

Figure 12:
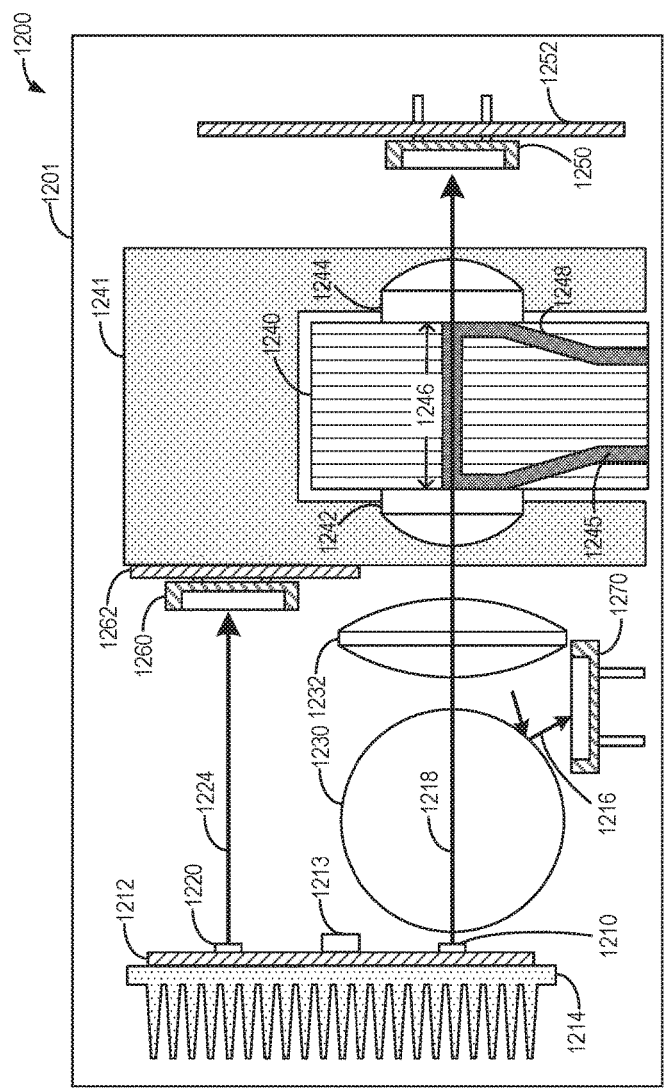
FIG. 12 illustrates an embodiment of a UV-VIS detector unit that includes a primary signal detector and a secondary detector for measuring light that is back-reflected by a sample.

It may be beneficial to include additional signal detectors in the UV-VIS detector unit to enable additional features and detector flexibility. Turning to FIG. 12, UV-VIS detector unit 1200 includes a housing 1201 and is shown including a primary signal detector 1250, a reference detector 1260, and a secondary signal detector 1270. Secondary signal detector 1270, positioned off-axis from an optical path of a first light source 1210, may measure light 1216 that is backscattered or reflected by coupling optics, such as a first lens 1230 and a second lens 1232, the walls of the detector unit housing 1201, or other components. Light 1216 may originate as a portion of light emitted by first light source 1210 that is reflected back through a flow cell 1240 instead of exiting flow cell 1240 through a second lens 1244. This back-reflected light 1216 may be used to extend the detection range of detector unit 1200 in order to detect smaller concentrations of a sample 1245 than can be detected using primary signal detector 1250. For example, the back-reflected light may travel through a sample-interrogating pathlength 1246 of flow cell 1240 twice, thereby increasing the absorbance of sample 1245 due to the directly proportional relationship between pathlength and absorbance according to the Beer-Lambert law. Therefore, small deviations in the reflectance signal measured by secondary signal detector 1270 may be amplified due to the logarithmic nature of the absorbance calculation, $A=-\log_{10}(T)$, to detect changes in sample absorbance at low concentrations.

In some examples, such as where a second light source 1220 and a reference detector 1260 are omitted, secondary signal detector 1270 may serve as the reference detector during a first operating mode and may measure sample reflectance during a second operating mode, as further described with respect to FIG. 20.

Detector unit 1200 includes the flow cell 1240 defined by a housing 1241 and including a first lens 1242, second lens 1244, and a capillary 1248 configured to flow the sample 1245 through the sample-interrogating pathlength 1246; substrates to which the light sources and detectors are coupled (e.g., substrates 1212, 1262, and 1252); and temperature sensors coupled to each substrate (e.g., sensor 1213).

Figure 13:
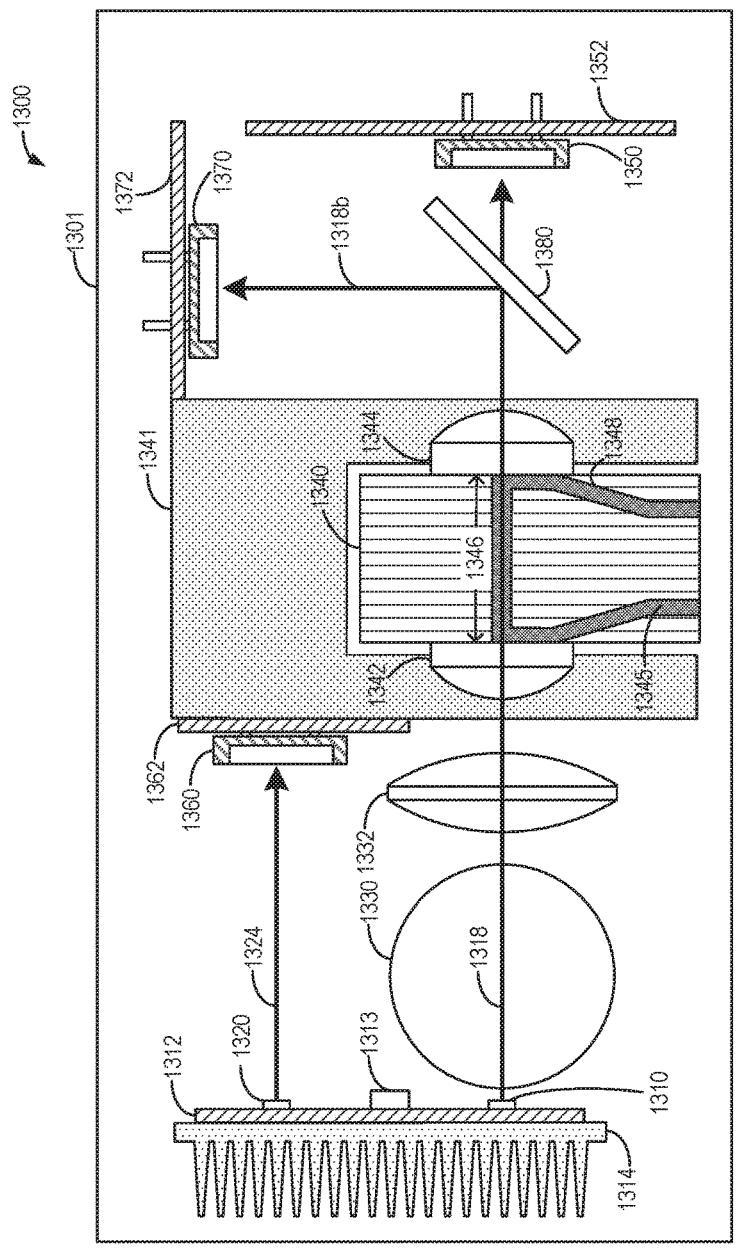
FIG. 13 shows an embodiment of a UV-VIS detector unit that enables simultaneous absorbance and fluorescence measurements.

FIG. 13 shows an example UV-VIS detector unit 1300 that includes a housing 1301, a signal detector 1350 as a first signal detector, and a signal detector 1370 as a second signal detector. Unlike the example of FIG. 12, wherein signal detector 1270 is a secondary signal detector that may also be used as the reference signal detector (e.g., during the first operating mode), second signal detector 1370 is a dedicated sample signal detector. After light in a light path 1318 passes through a sample 1345 and exits a flow cell 1340, a beam splitter 1380 directs a portion of light to second signal detector 1370 via a light path 1318b. In particular, second signal detector 1370 may measure a sample fluorescence signal from light path 1318b at the same time as first signal detector 1350 measures a sample transmittance signal from light path 1318. Fluorescence refers to a molecular absorption of light at a first wavelength and its nearly instantaneous re-emission at a second, longer wavelength. For example, as sample 1345 absorbs light of the first wavelength emitted by first light source 1310, electrons in the sample may move to a higher energy, excited state. As the electrons relax back down to their lower energy, ground state, energy is released as a photon of light at the second, longer wavelength. Thus, first signal detector 1350 may be configured to detect light of the first wavelength, and second signal detector 1370 may be configured to detect light of the second, longer wavelength.

The simultaneous measurement of light transmittance by first signal detector 1350 and sample fluorescence by second signal detector 1370 enables time-matched absorbance and fluorescence values to be obtained. As fluorescence is more sensitive than absorbance, the fluorescence measurement may enable lower concentrations of analyte to be detected than using absorbance measurements. However, not all analytes are fluorescent, which depends on the chemical structure of the molecule. For example, delocalized electrons (e.g., conjugated double bonds and aromatic groups) facilitate fluorescence. Further, while absorbance is given in absolute units, fluorescence units are arbitrary. In order to determine the concentration of the analyte using fluorescence, a standard curve of the analyte may be utilized. Therefore, it may be beneficial to continue absorbance measurements instead of measuring sample fluorescence only, for example, to discriminate between co-migrating peaks, such as if contaminating compounds were present whose absorption spectra overlap the absorption spectrum of the compound of interest.

Detector unit 1300 includes the flow cell 1340 defined by a housing 1341 and including a first lens 1342, a second lens 1344, and a capillary 1348 configured to flow the sample 1345 through a sample-interrogating pathlength 1346; first signal detector 1350 coupled to a substrate 1352; second signal detector 1370 coupled to a substrate 1372; a reference detector 1360 coupled to a substrate 1362; and temperature sensors coupled to each substrate (e.g., sensor 1313). Further, optional coupling optics may be included, such as a first lens 1330 and a second lens 1332.

Figure 14:
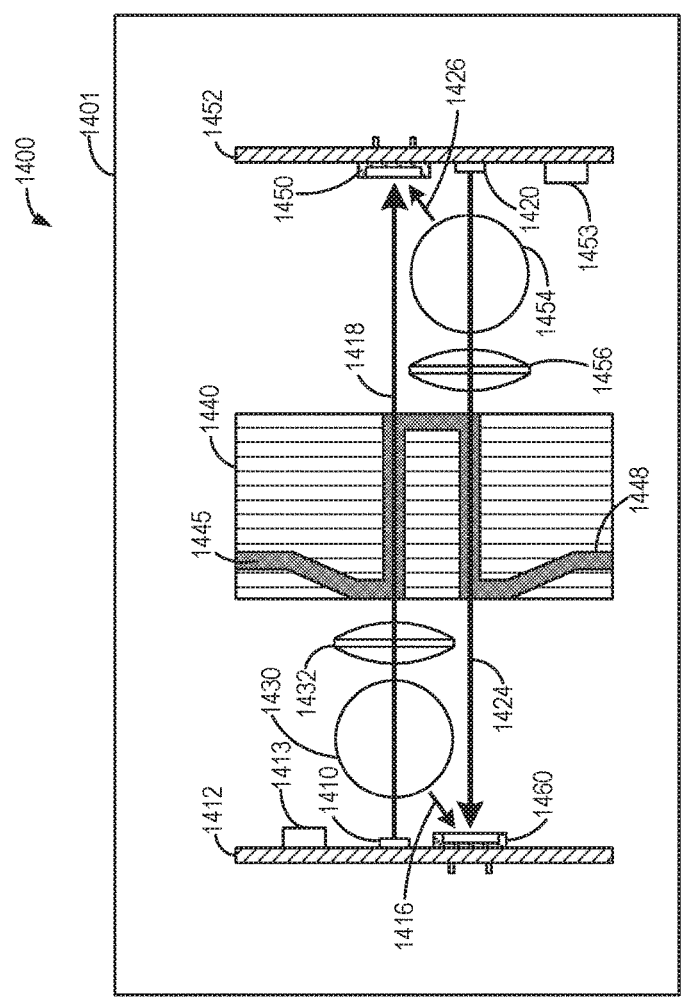
FIG. 14 shows an embodiment of a UV-VIS detector unit comprising a flow cell with multiple sample flow paths.

FIG. 14 shows an example embodiment of a multi-pass flow cell 1440 in a UV-VIS detector unit 1400 that includes a housing 1401. Light emitted by a first light source 1410 may pass through a first flow path of multi-pass flow cell 1440 in a light path 1418 before reaching a first signal detector 1450, and light emitted by a second light source 1420 may pass through a second flow path of multi-pass flow cell 1440 in a light path 1424 before reaching a second signal detector 1460. Further, coupling optics may be provided for each light source. Light in light path 1418 is shown passing through a first lens 1430 and a second lens 1432 of first light source 1410 before entering flow cell 1440. Light in light path 1424 is shown passing through a first lens 1454 and a second lens 1456 of second light source 1420 before entering flow cell 1440. In other examples, the coupling optics may be omitted.

Further, first light source 1410 and second signal detector 1460 are shown coupled to a first substrate 1412, which also includes a first temperature sensor coupled thereto. Second light source 1420 and first signal detector 1450 are shown coupled to a second substrate 1452, which also includes a second temperature sensor 1453 coupled thereto. In other examples, first light source 1410 and second light source 1420 may be coupled to first substrate 1412, similar to arrangement 600 of FIG. 6A, and first signal detector 1450 and second signal detector 1460 may be coupled to second substrate 1452. In still other examples, multi-pass flow cell 1440 may include additional flow paths and corresponding light sources and detectors.

Figure 18:
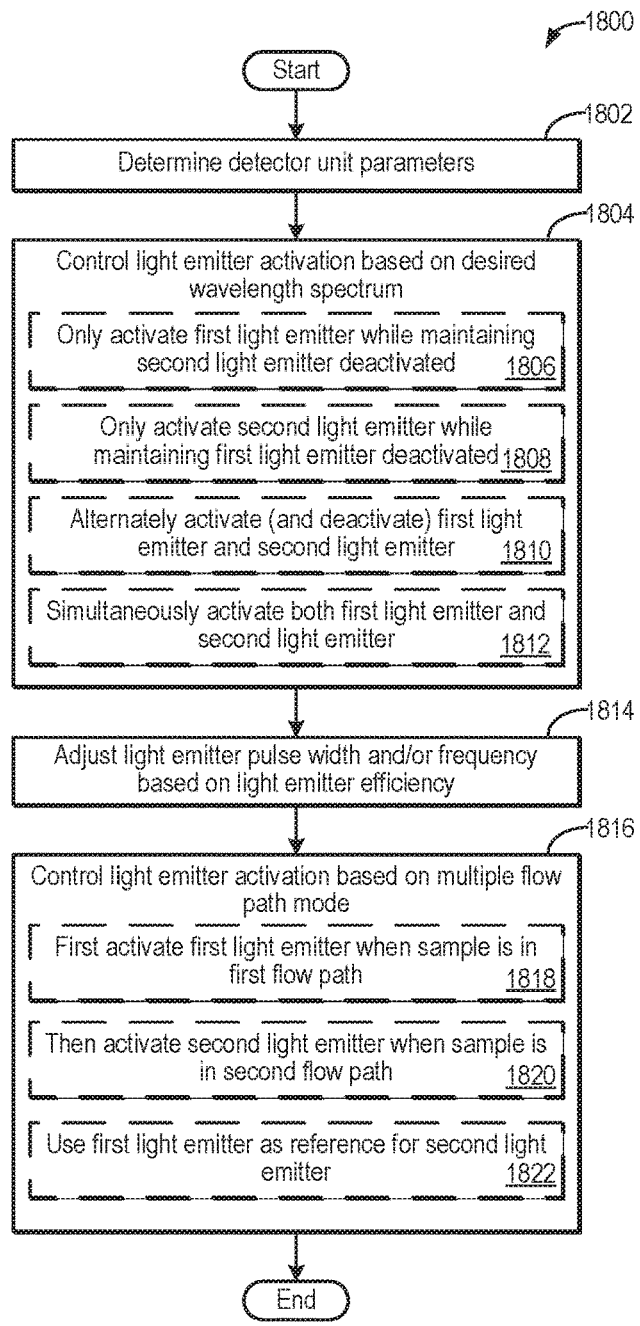
FIG. 18 is an example method for controlling multiple emitters of a light source.

In some examples, first light source 1410 and second light source 1420 may be controlled in such a way that second light source 1420 serves as a reference for first light source 1410, and vice versa, as further described with respect to FIG. 18. For example, first light source 1410 and second light source 1420 may be activated simultaneously while a sample 1445 is in the first flow path, with first light source 1410 interrogating the sample and second light source 1420 providing the reference beam. Then, first light source 1410 and second light source 1420 may again be activated simultaneously while sample 1445 is in the second flow path, with second light source 1420 interrogating the sample and first light source 1410 providing the reference beam.

In other examples, such as when coupling optics are present, first light source 1410 and second light source 1420 may each provide their own reference beam through light backscattered or reflected by the coupling optics, such as described with respect to FIGS. 2-4. For example, a light beam 1416 emitted by first light source 1410 and reflected by first lens 1430 may be measured by second signal detector 1460, particularly while second light source 1420 is off. Similarly, a light beam 1426 emitted by second light source 1420 and reflected by first lens 1454 may be measured by first signal detector 1450, particularly while first light source 1410 is off.

It may be advantageous for the light source(s) of the UV-VIS detector unit to be modular. In one example embodiment, the modular light source may be an LED-based system or a laser diode-based system that has been adapted to fit an existing UV-VIS detector unit as a replacement for a traditional deuterium lamp. In another example embodiment, a single wavelength LED-based system may be configured such that illumination modules with emitters of different wavelengths or other optical characteristics may be installed based on the analyte of interest. For example, such a modular system may allow the bulk of the UV-VIS detector unit to remain fixed and in place, allowing a single, configurable detector to analyze a broad range of substrates by switching out the light source module. In this way, additional detection capabilities may be added by an operator of the HPLC system as needed, lowering the cost of the system as well as the physical size.

Figure 15B:
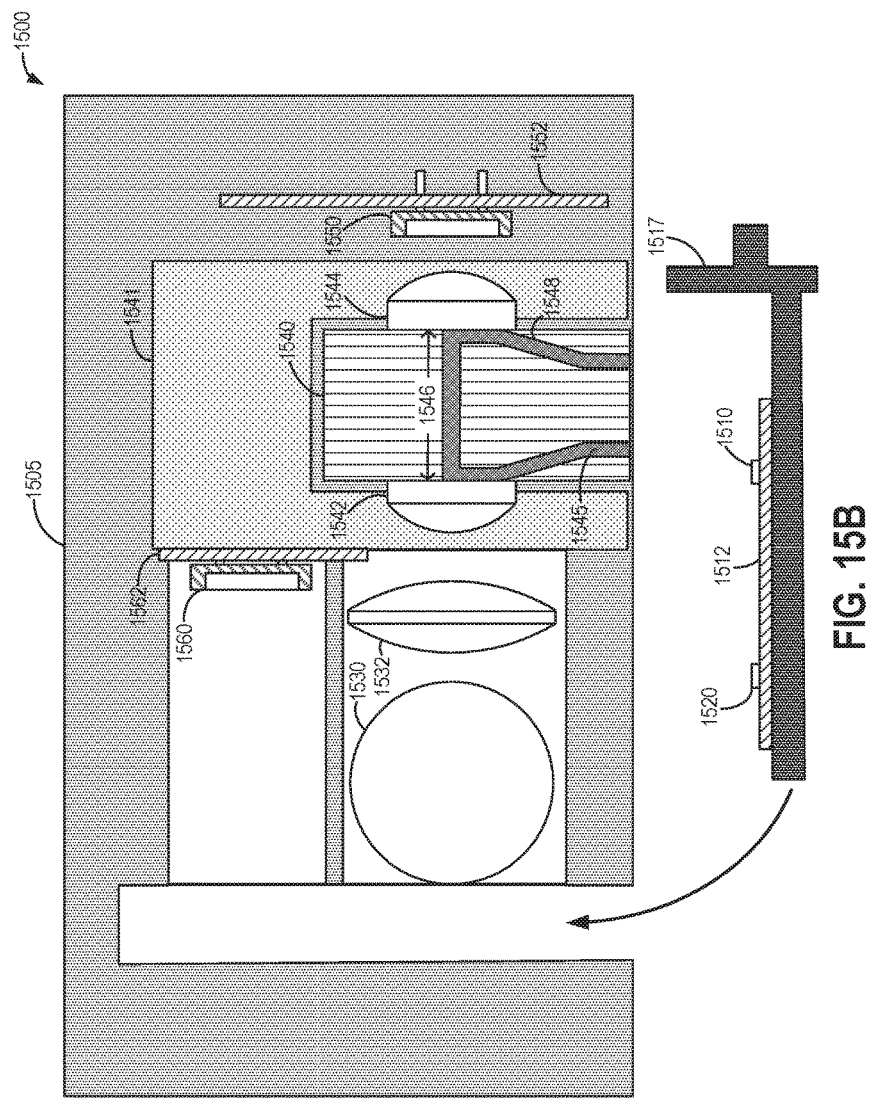

FIGS. 15A-15B illustrate an example embodiment of a modular UV-VIS detector unit 1500 that may be included in an HPLC system. Although the configuration of FIGS. 15A-15B is given as an example, any of the light source and detector configurations described herein, such as those described with respect to FIGS. 2-14, may be configured such that at least the signal/sample interrogating light source (also referred to as the primary light source) is modular.

A first light source 1510 and a second light source 1520, which may each include a plurality of light emitters, are shown coupled to a common substrate 1512, which is mounted to a removable module 1517. In FIG. 15A, removable module 1517 is shown inserted into a detector unit housing 1505 with suitably precise positioning to align first light source 1510, and therefore a light path 1518 of light emitted by first light source 1510, with a first lens 1530, a second lens 1532, a sample interrogation flow path of a flow cell 1540, and a signal detector 1550. Similarly, second light source 1520, and therefore a light path 1524 emitted by second light source 1520, may be aligned with a reference detector 1560. For example, removable module 1517 and detector unit housing 1505 may each include mechanical alignment features to prevent incorrect installation and facilitate the precise alignment. Further, removable module 1517 and/or detector unit housing 1505 may include retention features, such as snap-fit connectors, to secure removable module 1517 in place as well as allow installation and removal without the use of tools (e.g., an HPLC system operator may install or remove the module using his or her hands). In contrast, the other components of the detector unit, such as the flow cell, coupling optics, signal detector, and/or reference detector, may be fixedly coupled to the housing 1505. As used herein "fixedly coupled" may include the components being fixed to the housing such that the components cannot be removed without the use of tools (e.g., the components cannot be removed by hand). Further, the fixedly coupled components of the detector unit may be inaccessible to an operator while the housing is intact (e.g., to access the fixedly-coupled components, one or more walls of the housing may be removed).

Removable module 1517 may achieve an electrical connection with the fixed portion of UV-VIS detector unit 1500 when inserted, such as in FIG. 15A, through a connector mounted on wires, a connector mounted on a bulkhead or fixed panel, or via spring contacts. In one example, a portion of a circuit board or substrate of the UV-VIS detector unit 1500 includes a slot for a "card edge" connection with corresponding electrical connections on removable module 1517. Such a card edge connection may also facilitate proper positioning of removable module 1517 within detector unit housing 1505.

In some examples, removable module 1517 may include integral thermal management features (e.g., thermal systems), such as cooling fins or other thermally active surfaces that are built into the module. In this way, the thermal systems may be customized for the specific light source of each module. For example, higher efficiency light sources may be coupled to lower cost heatsinks, and lower efficiency light sources may be coupled to higher performance and higher cost heatsinks. Further, detector unit housing 1505 may house a common cooling fan that may be used by all modules. In another example, the cooling fan may be incorporated into the detector unit housing.

In FIG. 15B, removable module 1517 is shown removed from detector unit housing 1505. As such, no light is emitted from first light source 1510 and second light source 1520 due to a lack of an electrical connection.

In some embodiments, a plurality of emitters may be included in first light source 1510 and second light source 1520 in removable module 1517, such as shown in arrangement 600 of FIG. 6A. An emitter to be used for each light source may be selected by a user of the HPLC system, for example, based on the rotational or longitudinal installation position, via a physical actuator, or via motor-driven positioning. This may enable further detector customization without changing light source modules.

Detector unit 1500 includes flow cell 1540 defined by a housing 1541 and including a first lens 1542, second lens 1544, a capillary 1548 configured to flow a sample 1545 through a sample-interrogating pathlength 1546; signal detector 1550 coupled to a substrate 1552, and reference detector 1560 coupled to a substrate 1562. Further, optional coupling optics may be included, such as first lens 1530 and second lens 1532, as well as temperature sensors coupled to each substrate.

An additional configuration for a UV-VIS detector unit 1600 that includes a single light source is shown in FIG. 16. UV-VIS detector unit 1600 includes a housing 1601 and a beam splitter 1680 positioned between a light source 1610 and a first lens 1630. Beam splitter 1680 directs a portion of light emitted by light source 1610 to reference detector 1660 via a light path 1618b while the remaining portion of light remains in a light path 1618. Thus, the light of light path 1618b provides the reference beam. Detector unit 1100 also includes a flow cell 1640 defined by a housing 1641 and including a first lens 1642, a second lens 1644, and a capillary 1648 configured to flow a sample 1645 through a sample-interrogating pathlength 1646; a signal detector 1650 coupled to a substrate 1652; and the reference detector 1660 coupled to a substrate 1662. Light source 1610 is shown coupled to a substrate 1612, which is coupled to a thermal device 1614. A temperature sensor may optionally be coupled to each substrate, such as temperature sensor 1613 coupled to substrate 1612. Further, optional coupling optics may be included, such as a first lens 1630 and a second lens 1632.

Turning to FIG. 17, a high-level flow chart of an example method 1700 for determining an absorbance of a sample using a UV-VIS detector unit, such as the detector units described with respect to FIGS. 1-5 and FIGS. 7-16, is shown. For example, the detector unit may be included in an HPLC system, such as HPLC system 100 of FIG. 1, to analyze the sample after it is eluted from a column. The UV-VIS detector unit may include a single light source, such as the detector units described with respect to FIGS. 2-5 and FIG. 16, or multiple light sources, such as the detector units described with respect to FIGS. 7-15. Method 1700 and the rest of the methods included herein may be executed by a controller, such as the controller of control system 110 of FIG. 1, based on instructions stored on a memory of the controller and in conjunction with signals received from the UV-VIS detector unit.

Method 1700 begins at 1702 and includes activating a first light source to transmit light through a sample. As mentioned above, in some examples, the UV-VIS detector may include one light source, and thus, the first light source is the only light source of the UV-VIS detector unit (e.g., light source 210 of FIG. 2). In other examples, the UV-VIS detector may include multiple light sources, and the first light source is a light source that shares a common axis with a flow path for interrogating the sample within a flow cell (e.g., first light source 710 of FIG. 7). In either case, the first light source may include one or more emitters. Therefore, at 1703, method 1700 optionally includes controlling the activation of multiple emitters of the first light source, as further described with respect to FIG. 18. In this way, a desired illumination wavelength or wavelength spectrum may be achieved. The first light source may be activated at a predetermined duty cycle to provide a desired light intensity (e.g., optical power output), for example.

At 1704, method 1700 optionally includes activating a second light source. If included in the detector unit, the second light source (e.g., second light source 720 of FIG. 7) may provide a reference beam for the first light source. In other examples, particularly those in which the detector unit does not include a second light source, the first light source may provide its own reference beam, as described further below. The second light source may be activated at a predetermined duty cycle to provide a desired light intensity, which may be the same or different than the predetermined duty cycle used to activate the first light source, just as the second light source may be similar or dissimilar to the first light source.

At 1706, method 1700 includes measuring light (from the first light source) transmitted through the sample via a signal detector. As described above with respect to FIG. 2, the signal detector may measure the intensity of light that passes through the sample and output a corresponding voltage signal to the controller. The output voltage signal may be referred to as a "sample transmittance signal."

At 1708, method 1700 includes measuring the reference beam via a reference detector. As described above (e.g., at 1704) the reference beam may be generated by the second light source or by the first light source (e.g., using a beam splitter, a reflector, or back-scatter from a housing, components, and/or coupling optics), depending on the UV-VIS detector unit configuration. The reference beam includes light that has not been transmitted through the sample. Similar to the signal detector, the reference detector may output a voltage signal to the controller relative to the intensity of light measured by the reference detector, which may be referred to as a "reference signal."

At 1710, method 1700 includes determining detector unit parameters. Detector unit parameters may include the intensity of the first light source and/or the second light source, a temperature at a location of interest (as measured by a temperature sensor, such as temperature sensor 713 of FIG. 7), an electrical current driving the first light source and/or the second light source, an electrical voltage across the first light source and/or the second light source, etc. The location of interest may be near the first light source, at the flow cell, near the signal detector, or at a thermal device, for example.

The intensity of each light source may be determined based on the measured parameters (e.g., electrical drive current, pulse width of activation, and temperature) and known characteristics of the light source or may be directly measured using a signal detector. Additionally, an optimal region for driving each light source may be determined. For example, the optimal region may be within limits of electrical current density of a particular light source, or based on the elapsed time since power was applied and a known starting temperature of the light source in order to drive the light source in a known temperature range. The known temperature range may not be measured directly, but may have been previously characterized, such as by using thermal structure functions to determine thermal time constants of the system. For example, the controller may input the limits of electrical current density, elapsed time since power was applied, and the starting temperature of the light source into a look-up table and output the optimal region for driving the light source.

At 1712, method 1700 optionally includes controlling the first light source intensity based on the detector unit parameters (e.g., as determined at 1710). For example, the intensity of the first light source may be controlled to maintain a desired output level. In one example, the first light source intensity may be controlled using a first closed-loop strategy wherein the temperature of the first light source is used as a feedback parameter. In a second example, the first light source intensity may be controlled using a second closed-loop strategy wherein the light intensity of the first light source is used as a feedback parameter. In a third example, the control method may be implemented using analog electronics, without use of a digital controller. Example electronics that may be used to perform the light source intensity control described herein will be explained in more detail below with respect to FIG. 30. In another example, the first light source intensity may be controlled using a third closed-loop strategy wherein proportional-integral-derivative (PID) control, adaptive control, and/or gain scheduling are utilized. In a further example, an open-loop strategy may be employed wherein the intensity of the first light source is adjusted using a correction factor based on a calibration function that incorporates characteristics of the first light source and a thermal system (e.g., thermal device 714 of FIG. 7) coupled to the first light source.

As one example, such as where the first light source comprises an LED, the LED may be operated at a constant drive current where the heat load from the LED is higher than the thermal system can dissipate in order to achieve an optimal LED temperature. In such an example, the output of the LED may reach a peak, and then decrease as the device temperature rises until thermal equilibrium is reached. In another example, each light source may have a known thermal capacitance response. More photons may be emitted by the light source when it is cold. Therefore, by pulsing the light source at a low duty cycle with a high repetition rate, wherein the pulse width is shorter than a thermal time constant of the device, a higher peak light intensity will be output (e.g., an average photon flux rate is higher) without an associated heating of the light source that would otherwise persist in a continuous wave mode of operation. This may also prolong the life of the light source, may allow higher sensitivity, or may enable measurement of more concentrated samples.

Figure 23:
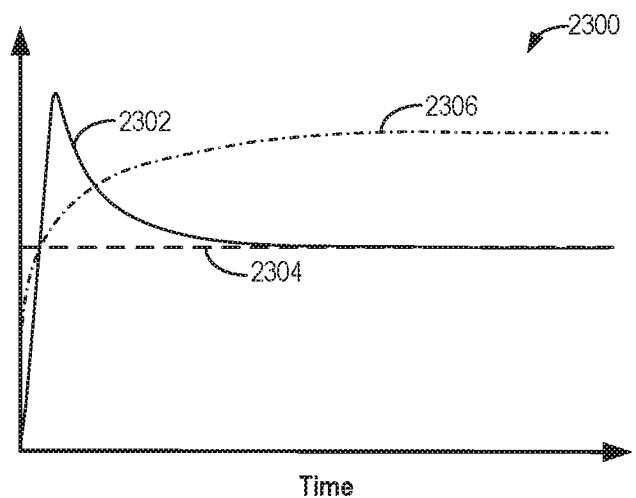
FIG. 23 shows an example graph of a power output and temperature of a light emitter over time.

Turning briefly to graph 2300 FIG. 23, output (plot 2302) and temperature (plot 2306) of a light emitter over time (the X-axis) is shown. When the light emitter is turned on, light emitter output (plot 2302) increases steeply initially until a peak output is reached. As the light emitter remains on, the light emitter output decreases exponentially as the light emitter heats up (e.g., the temperature increases asymptotically, as shown in plot 2306), until a steady state light output (dashed line 2304) is reached as the operating temperature reaches thermal equilibrium (e.g., the temperature remains relatively constant). However, operating at steady state may decrease the average photon flux rate output by the light emitter and decrease the stability of the beam emitted by the light emitter.

Figure 25:
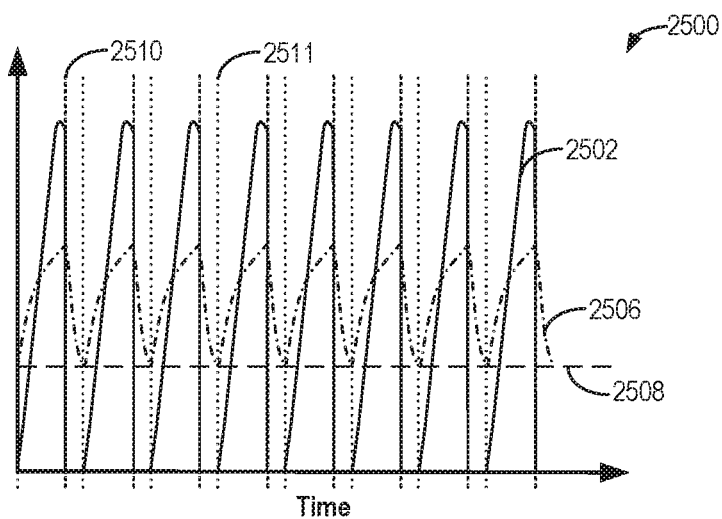
FIG. 25 shows an example graph of light emitter power output and temperature during a pulsed mode of operation.

Continuing to FIG. 25, a graph 2500 of light emitter output (plot 2502) and temperature (plot 2506) over time (the X-axis) during a pulsed mode (e.g., strobed mode) of light emitter operation is shown. In the pulsed mode of operation, the light emitter is switched on (indicated by half-dashed lines 2510) and then off (indicated by dotted lines 2511) before thermal equilibrium is reached. In the example of graph 2500, a peak light emitter output is reached, and then output begins to decrease (plot 2502), similar to plot 2302 of FIG. 23. The light emitter temperature (plot 2506) continues to increase from a starting temperature (dashed line 2508). However, the slight reduction in light emitter output power may be used as a trigger to switch off the light emitter, at which point the temperature (plot 2506) falls back to the starting temperature (dashed line 2508). When the system cools to the starting temperature, the light emitter is switched back on. Using the pulsed mode of operation, a significantly higher light emitter output during the "on" portion of the cycle at a given drive current and light emitter lifetime can be achieved than if thermal equilibrium is reached. This may enable very low-output emitters, such as a 235 nm LED, to be used in applications where the achievable continuous (e.g., steady state) power for an acceptable degradation rate (lifetime) would disqualify the device.

Alternatively, the system temperature may be used to trigger the switch off. For example, the light emitter may be switched off before a thermal time constant is reached. The thermal time constant may be defined as the time for a system to reach a percentage of a temperature difference between a final asymptotic ending temperature value and a starting temperature value. Any percentage may be selected, although 63.2% (derived from 1−1/e in a natural logarithmic response to a step input) and 90% are common examples. The thermal time constant is a characteristic of the thermal system, which includes contributions from parameters such as thermal mass of each component, thermal diffusivity of each component, thermal conductivity of each component, thermal resistance at each interface, etc.

In another example, the drive current may be reduced when the light emitter output reaches a set value such that the current level is modulated to achieve constant light output even as the system temperature rises to equilibrium. For example, if two LEDs are connected electrically in series, the electrical current I through each device is the same. If the LEDs are connected to a common thermal substrate and a first temperature T1 is measured at time t1 and second, higher temperature T2 is measured at a later time t2, the controller may reduce the current such that at a further later time t3, the temperature is driven back toward T1, which may be a desired temperature.

Figure 26:
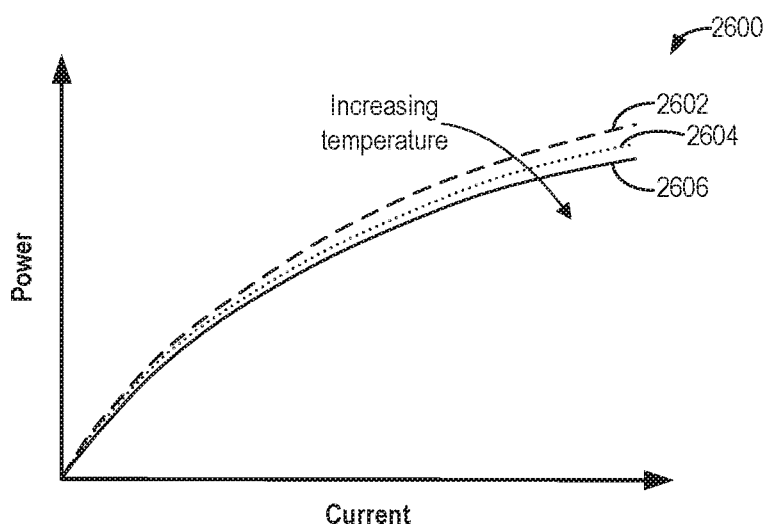
FIG. 26 shows an example graph showing an example relationship between light emitter current and power at three different operating temperatures.
Figure 27:
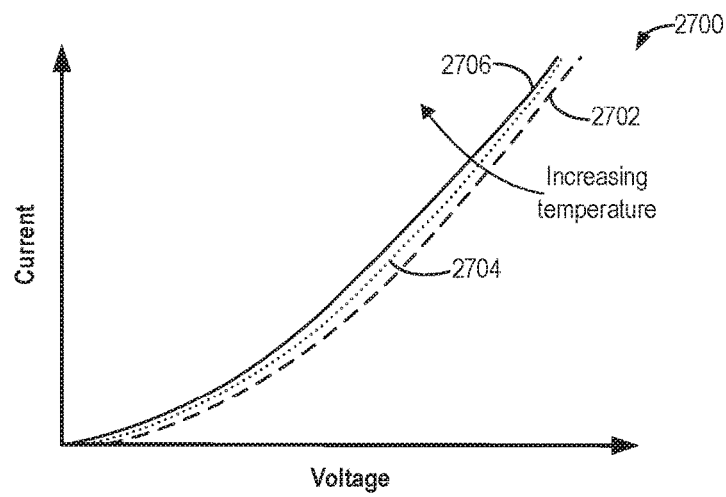
FIG. 27 shows an example graph showing an example relationship between light emitter voltage and current at three different operating temperatures.
Figure 28:
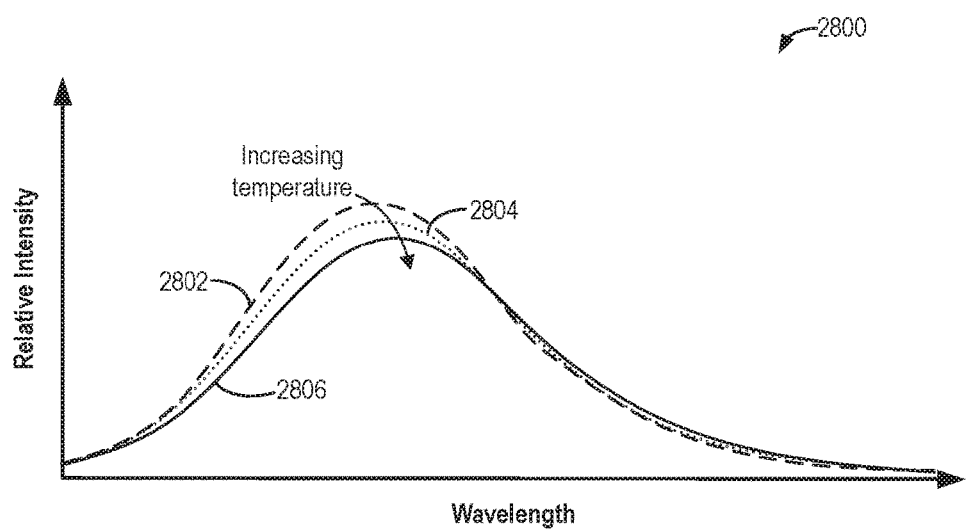
FIG. 28 shows an example graph showing an example relationship between an emission spectrum of a light emitter and a relative intensity of the emission at three different operating temperatures.

FIGS. 26-28 show example LED power, current, voltage, temperature, and wavelength relationships. Any of these measured parameters combined with a pre-measured characteristic curve (such as the curves shown in FIGS. 26-28) may be used to adjust one of the other dependent parameters.

Turning first to FIG. 26, graph 2600 shows an example relationship between current (X-axis) and power (Y-axis) of an LED. Generally, as the current increases, the power increases in a non-linear fashion (e.g., asymptotically). Plot 2602 (dashed line) corresponds to the current and power relationship measured at a first temperature (e.g., 30° C.). Plot 2604 (dotted line) corresponds to the current and power relationship measured at a second temperature, higher than the first (e.g., 50° C.). Plot 2606 (solid line) corresponds to the current and power relationship measured at a third temperature, higher than the second (e.g., 70° C.). As the temperature of the LED increases, the current versus power curve shifts so that the power output at a given current decreases. Thus, for a given drive current, the temperature of the LED may be modulated in order to change the power output by the LED.

Continuing to FIG. 27, graph 2700 shows an example relationship between voltage (X-axis) and current (Y-axis) of an LED, which may be the same LED as in FIG. 26, for example. Generally, as voltage increases, current increases in a non-linear fashion (e.g., exponentially). Similar to graph 2600 of FIG. 26, plot 2702 (dashed line) corresponds to the voltage and current relationship measured at the first temperature, plot 2704 (dotted line) corresponds to the voltage and current relationship measured at the second temperature, and plot 2706 (solid line) corresponds to the voltage and current relationship measured at the third temperature. As the temperature of the LED increases, the voltage versus current curve shifts so that the LED current at a given voltage increases. Thus, by changing the temperature of the LED, the current or voltage of the LED may be changed.

Turning next to FIG. 28, graph 2800 shows example emission spectra of an LED (which may be the same LED as in FIGS. 26 and 27) at different operating temperatures. Wavelength is shown along the X-axis, and relative intensity is shown along the Y-axis. Similar to graph 2600 of FIG. 26 and graph 2700 of FIG. 27, plot 2802 (dashed line) corresponds to the emission spectrum measured at the first temperature, plot 2804 (dotted line) corresponds to the emission spectrum measured at the second temperature, and plot 2806 (solid line) corresponds to the emission spectrum measured at the third temperature. Generally, the relative intensity of light emitted by the LED varies with wavelength. For each curve, the wavelength corresponding to the greatest relative intensity may be referred to as a wavelength of maximum emission. As the temperature of the LED increases, the emission spectrum shifts. For example, the maximum relative intensity decreases and the wavelength of maximum emission shifts to a longer wavelength (e.g., a bathochromic shift) as the temperature increases. Thus, wavelength of maximum emission may be modulated by changing the temperature of the LED.

Returning to FIG. 17, at 1714, method 1700 includes calculating a reference correction based on the reference signal and/or detector unit parameters. If the first light source is used as its own reference, the backscattered or reflected light measured by the reference detector may exhibit identical or near-identical intensity fluctuations as the light transmitted through the sample and measured by the signal detector, since the backscattered or reflected light is emitted from the same light source as the light transmitted through the sample. As such, fluctuations in the reference signal may be directly used to determine intensity fluctuations in the first light source without further correlation. In one example, a correction factor, C, may be given by: $C_t = I_{REF\_0}/I_{REF(t)}$, where $I_{REF\_0}$ is the reference signal at an initial time point (e.g., when the first light source is initially activated) and $I_{REF(t)}$ is the reference signal at a given time t.

In contrast, if a second light source is used as the reference, method 1700 may optionally include correlating the sample transmittance signal and reference signal fluctuations, as indicated at 1715. Further, parameters that may be correlated to intensity fluctuations in light emitted by the first light source include a temperature at a location of interest (e.g., near the signal or reference detector, at the flow cell, at a light source substrate, and/or at the thermal device), an electrical current driving the first light source or the second light source, an electric voltage across the first light source or the second light source, light source on-time, and boundary conditions (e.g., heat flux at a thermal interface). Such parameters may provide correction factors that, together, may constitute a correlation function, which may be linear or non-linear. The correlation function may be determined through calculations, simulations, laboratory measurements of a reference system, or in situ measurements of the UV-VIS detector unit, for example. Correlation function data may be stored in a look-up table, to which the controller may refer to determine $C_t$. Alternatively, the controller may apply the correlation function as a continuous mathematical formula (such as a linear, exponential, polynomial fit, etc.) to determine $C_t$.

At 1716, method 1700 includes applying the reference correction to the sample transmittance signal. For example, an intensity of transmitted light measured by the signal detector at time t, $I_{SIG(t)}$ may be transformed into a corrected intensity $I_{SIG(t)}^*$ according to: $I_{SIG(t)}^* = C_t \times I_{SIG(t)}$. In this way, data may be corrected for each time point individually.

At 1718, method 1700 optionally includes controlling the first light source intensity and/or signal detector gain based on the corrected sample transmittance signal. For example, if the corrected sample transmittance signal is high, such as when the sample is at a low concentration, the light intensity of the first light source may be decreased, as further described with respect to FIG. 19, in order to increase a dynamic range of the signal detector and more accurately detect low concentrations of the sample. In another example, when the signal detector measures a saturated signal, a secondary signal detector may be used to determine the sample transmittance signal, as further described with respect to FIG. 20, in order to further increase the dynamic range of the UV-VIS detector unit.

At 1720, method 1700 includes determining the absorbance of the sample and plotting data on a chromatogram. For example, the controller may perform a blank correction on the corrected sample transmittance signal, as described with respect to FIG. 2, to determine a light transmittance of the sample alone (without solvent) and may further convert the light transmittance to an absorbance value, which may then be plotted against time (and/or fraction number) on the chromatogram. At a given measurement time, the sample may contain no analytes (if only solvent is present) or a plurality of analytes. However, if the sample contains one analyte that is known, the concentration of the analyte may also be determined according to the Beer-Lambert law. In other examples, the concentration of total analyte present may be approximated using the absorbance of the sample and the Beer-Lambert relationship. Following 1720, method 1700 ends.

In this way, the absorbance (and thereby, concentration) of the sample may be accurately determined by correcting the sample transmittance signal (e.g., based on a reference beam measured by a reference detector as well as a blank correction) as well as dynamically controlling the light source(s) and the signal detector as needed, as further described herein. Further, in example detector unit configurations where a detector is mounted on a common substrate with a light source (e.g., detector 460 of FIG. 4), the temperature fluctuations caused by activation/deactivation and/or cooling of the light source may affect output from the detector. In such examples, the temperature of the substrate and/or detector may be determined (e.g., from a temperature sensor), and the output form the detector may be adjusted. For example, a detector gain may be adjusted based on the temperature.

FIG. 18 shows an example method 1800 for controlling a light source that comprises a plurality of light emitters, such as first light source 610 of FIG. 6A, in a UV-VIS detector unit, and/or controlling multiple light sources in a single detector unit, such as in the multiple-flow path configuration of FIG. 14, each of which may be included in an HPLC system. Including multiple light emitters in the light source may enable spectral customization of the light source based on a sample to be analyzed. For example, different samples (or analytes within a single sample) may have different wavelengths of maximal absorption.

Method 1800 begins at 1802 and includes determining detector unit parameters. Detector unit parameters may include the intensity of the light source, relative efficiencies of each light emitter (e.g., relative to each other), a temperature at a location of interest, an electrical current driving the light source, an electrical voltage across the light source, etc. The location of interest may be near the light source, at a flow cell, near a signal detector, or at a thermal device coupled to the light source, for example. The intensity of the light source may be determined based on the measured parameters (e.g., electrical drive current, pulse width of activation, and temperature) and known characteristics of the light source or may be directly measured. Other detector parameters may include user-selected parameters, such as desired wavelength of output light.

At 1804, method 1800 includes controlling light emitter activation based on a desired wavelength spectrum. The desired wavelength spectrum may be chosen based on an analyte of interest. For example, a single wavelength of 254 nm may be chosen for detecting aromatic compounds. In another example, a broad wavelength spectrum may be chosen for obtaining an absorbance profile of an unknown compound. In a first example, controlling light emitter activation based on the desired wavelength spectrum includes only activating a first light emitter (e.g., an LED that emits 254 nm light) while maintaining a second light emitter deactivated, as indicated at 1806. In a second example, controlling light emitter activation based on the desired wavelength spectrum includes only activating the second light emitter (e.g., an LED that emits 488 nm light) while maintaining the first light emitter deactivated, as indicated at 1808. In a third example, controlling light emitter activation based on the desired wavelength spectrum includes alternately activating (and deactivating) the first light emitter and the second light emitter, as indicated at 1810. By alternating between the first light emitter and the second light emitter, a controller may determine a ratio of the two absorbance peaks (one for each light emitter wavelength), which may be used to further distinguish one analyte from another. In a fourth example, controlling light emitter activation based on the desired wavelength spectrum includes simultaneously activating both the first light emitter and the second light emitter, as indicated at 1812, to produce a multi-wavelength spectrum of illumination. For example, the resulting signal may have an intensity proportional to the product of the intensities of the first light emitter and the second light emitter, and its frequency proportional to a frequency difference between the first light emitter and the second light emitter (e.g., a beat frequency). Note that while the above examples are given for two light emitters, more than two light emitters may be included and controlled similarly. Furthermore, the methods described herein for modulating the multiple light sources may be utilized in the systems described above with respect to FIGS. 1-16 and/or the methods may be used in systems with additional or alternative components, such as detector unit configurations that include integrating chambers (e.g., where the light source(s) are assembled directly into the mechanical construction of the flow cell), waveguides, fiber couplers, beam splitters, etc.

At 1814, method 1800 includes adjusting the light emitter pulse width and/or frequency based on the light emitter efficiency. For example, a blue green-emitting (e.g., 488 nm) LED has a higher quantum efficiency (e.g., higher optical power output for a given electrical power input) than a UV-emitting (e.g., 254 nm) LED. Thus, the UV-emitting LED may be activated with a greater pulse-width and/or duty cycle than the blue green-emitting LED in order to output the same optical power.

At 1816, method 1800 includes controlling light emitter activation based on a multiple flow path mode. For example, the multiple flow path mode may be used for a flow cell with more than one sample interrogation flow path, such as flow cell 1440 of FIG. 14. Controlling light emitter activation based on the multiple flow path mode includes activating the first light emitter when the sample is in a first flow path, as indicated at 1818, and then activating the second light emitter when the sample is in a second flow path as indicated at 1820. The first light emitter and the second light emitter may be included in separate light sources (e.g., a first light source and a second light source) in order to illuminate different flow paths. The timing of activation for the first light emitter and the second light emitter may be coordinated based on the flow rate of the HPLC system, for example. A controller may input the flow rate into a look-up table or equation and output the corresponding timing of activation, for example. The method may further include using the first light emitter as a reference for the second light emitter (and vice versa), as indicated at 1822. As described with respect to FIG. 6A, in some examples, each emitter in the first light source may have a dedicated reference emitter in the second light source. The first light emitter (e.g., in the first light source) and the second light emitter (e.g., in the second light source) may be pulsed simultaneously, with the first light emitter interrogating sample in the first flow path, and the second light emitter transmitting through solvent in the second flow path, for example. Method 1800 then ends.

FIG. 19 shows an example method 1900 for adjusting light source optical power and/or signal detector gain as a function of sample detector response in order to increase the concentration range of analyte that can be measured by a UV-VIS detector unit. For example, at low analyte concentrations, relatively little light may be absorbed, leading to a high transmittance signal, whereas at high analyte concentrations, a relatively large portion of the light may be absorbed as it passes through the sample, leading to a low transmittance signal. Both high and low sample concentrations may be outside of a linear range of the sample detector for determining sample absorbance.

Figure 24:
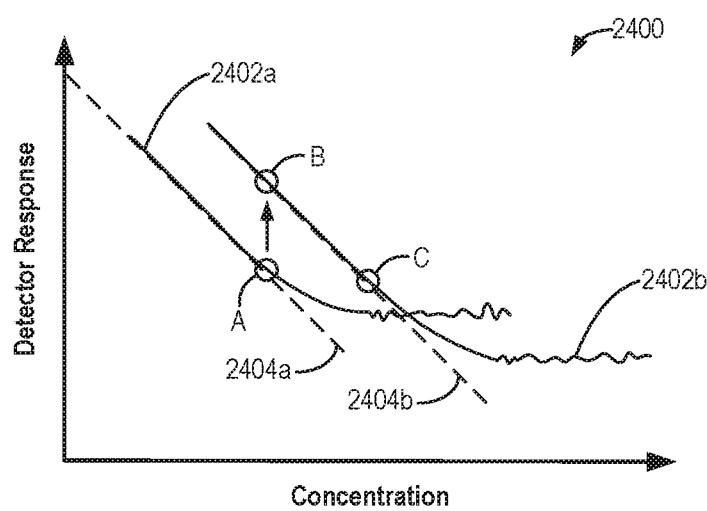
FIG. 24 shows an example graph depicting how a detector response curve may be shifted by increasing an intensity of a light source in order to extend a detection range to higher concentrations of analyte.

Turning briefly to FIG. 24, a graph 2400 of a relationship between detector response (the Y-axis) and sample concentration is shown (the X-axis) is shown. Plot 2402*a* shows a detector response curve at a first, lower light source intensity, and plot 2402*b* shows a detector response curve at a second, higher light source intensity. Dashed line 2404*a* represents an ideal detector response at the first, lower light source intensity, and dashed line 2404*b* represents an ideal detector response at the second, higher light source intensity. At point A on detector response curve 2402*a*, the measured detector response (plot 2402*a*) begins to deviate from the ideal detector response (dashed line 2404*a*). Thus, point A refers to a concentration that is too high for accurate measurement by the detector at the first, lower light source intensity. Therefore, the light source output and/or the detector gain may be adjusted, such as according to the methods described herein, in order to extend the dynamic range of the signal detector and the UV-VIS detector as a whole. In the example of FIG. 24, the light source intensity is increased to the second, higher light source intensity, which shifts the detector response curve (plot 2402*b*). Point B on detector response curve 2404*b* represents the same sample concentration as point A; however, with the second, higher light source intensity, the measured detector response (plot 2402*b*) does not deviate from the ideal detector response at the second, higher light source output (dashed line 2404*b*). For example, point B is within the linear range of the detector at the second, higher light source output. Further, at the second, higher light source output, the detector is able to accurately measure even higher concentrations of sample, such as up to point C.

However, it should be understood that at substantially high concentrations of sample (e.g., above 10 mM), the relationship between absorbance and concentration is not linear due to limitations of the Beer-Lambert law, which cannot be accounted for by adjusting light source output and/or detector gain. Data obtained at such high concentrations may exhibit a "clipped" appearance on the resulting chromatogram and may not represent changes in sample concentration.

Returning to FIG. 19, method 1900 begins at 1902 and includes obtaining a corrected sample transmittance signal, as described with respect to FIG. 17.

At 1904, method 1900 includes determining if the corrected sample transmittance signal is less than a first threshold. The first threshold may define a transmittance signal below which the detector response deviates from an ideal response. Further, below the first threshold, changes in light transmittance due to sample absorbance may be limited by a noise floor of the detector, which is primarily influenced by stray light, dark noise, electrical noise, and analog-to-digital quantization. For example, the corrected sample transmittance signal may be less than the first threshold when the concentration of the sample is high, resulting in high light absorption by the sample and little light transmittance.

If the corrected sample transmittance signal is determined to be less than the first threshold, method 1900 proceeds to 1906 and includes increasing the light source output and/or increasing signal detector gain. By increasing light source output (e.g., by increasing drive current/voltage, decreasing light source temperature, increasing light source duty cycle pulse width and/or frequency, and/or adjusting a neutral density filter, a variable attenuator, or an adjustable aperture or iris), the amount of light transmitted through the sample may increase. By increasing signal detector gain, the detector may become more sensitive to small changes in light intensity. Adjusting the detector gain allows more optimal utilization of the dynamic range of the signal processing electronics, such as an analog to digital converter. Another advantage of adjusting detector gain is it may allow the light source to be operated at an optical point, such as a constant temperature or a constant output mode. If the output is constant, the absorbance within the analyte is kept the same and potentially more closely adheres to the Beer-Lambert relationship, while the detector signal is moved into a more optimal position of the analog to digital converter's operating range. Following 1906, method 1900 may return to 1902. In this way, the light source output may be incrementally increased and/or the detector gain may be incrementally increased until the corrected sample transmittance signal is not less than the first threshold.

If the corrected sample transmittance signal is not less than the first threshold at 1904, method 1900 proceeds to 1908 and includes determining whether the corrected sample transmittance signal is greater than a second threshold, higher than the first threshold. The second threshold may define a transmittance signal above which the detector response deviates from the ideal response, such as when the signal detector becomes saturated. For example, the corrected sample transmittance signal may be greater than the second threshold when the concentration of the sample is low, resulting in little light absorption by the sample and high light transmittance.

If the corrected sample transmittance signal is greater than the second threshold, method 1900 proceeds to 1910 and includes decreasing the light source output and/or decreasing the signal detector gain. By decreasing the light source output, the amount of light received by the signal detector will decrease. This may enable the detector to more accurately measure small changes in light intensity. By decreasing the detector gain, the detector may operate in a more optimal portion of the analog to digital converter and electronics. Method 1900 may then return to 1902, as described above, enabling the light source intensity to be incrementally decreased and/or the detector gain incrementally decreased until the corrected sample transmittance signal is not greater than the second threshold.

If the corrected sample transmittance signal is not greater than the second threshold at 1908, method 1900 proceeds to 1912 and includes maintaining the light source output and/or the signal detector gain. For example, the corrected sample transmittance signal is between the first threshold and the second threshold, indicating that the detector response is within the linear range and does not deviate from the ideal detector response. Following 1912, method 1900 ends.

Some UV-VIS detector unit configurations may allow the dynamic range of the detector unit to be further extended to detect even lower concentrations of sample. For example, these configurations may include a primary detector (e.g., primary signal detector 1250 of FIG. 12), a secondary signal detector (e.g., secondary signal detector 1270 of FIG. 12), and a dedicated reference detector (e.g., reference detector 1260 of FIG. 12). In other examples, these configurations may include a reference detector that may also serve as the secondary signal detector (e.g., reference detector 260 of FIG. 2). In each example, the secondary signal detector is positioned to measure light that is back-reflected through the sample and scattered by coupling optics, a reflector (such as reflector 534 of FIG. 5, which may be included additionally or alternatively to the coupling optics), and/or adjacent non-optical components, such as a housing of the flow cell (e.g., flow cell housing 1241 of FIG. 12). Thus, coupling optics and reflectors need not be present for the secondary signal detector to receive back-reflected light from the sample.

FIG. 20 shows an example method 2000 for utilizing this back-reflected light to detect a presence and concentration of dilute analyte in the sample, which may be more sensitive than using the primary signal detector (even with the light source intensity and/or signal detector gain adjustments described with respect to FIG. 19) due to the increased pathlength of the back-reflected light, as further described with respect to FIG. 12.

While flowing through a flow cell of the UV-VIS spectrophotometer, each component of a sample is exposed to one or more wavelengths of light emitted from one or more light sources (e.g., deuterium lamps, mercury arc lamps, tungsten lamps, light-emitting diodes, and/or laser diodes). The light may be partially to fully absorbed by the component depending on the chemical structure and concentration of the component as well as the wavelength(s) of light used. Any unabsorbed light may pass through the flow cell and be transmitted to a signal detector (e.g., a variable-wavelength detector unit or a diode array detector unit). The amount of light absorbed may be proportional to the concentration of the component. When the concentration of the sample is low, a large amount of unabsorbed light may be transmitted to the signal detector, which may saturate the signal detector. In another example, fluctuations in light transmittance due to a low concentration of sample may be indistinguishable to fluctuations in light transmittance due to noise. Thus, low concentration samples may go undetected.

According to embodiments disclosed herein, a secondary signal detector may be used to measure back-reflected light from a sample in the flow path, enabling lower concentrations of sample to be detected than with a primary signal detector. As an example, during a first mode, a first absorbance of the sample in the flow path may be determined based on output from the primary signal detector, and during a second mode, a second absorbance of the sample the flow path may be determined based on output from the secondary signal detector. The first mode may include the primary signal detector receiving light from the first light source at a level below a saturation point of the primary signal detector. The second mode may include the primary signal detector receiving light from the first light source at a level above the saturation point of the primary signal detector, for example. In this way, in the second mode, back-reflected light from the sample that is measured by the secondary signal detector may be used when the primary signal detector is saturated, enabling lower concentrations of sample to be detected than by using the primary signal detector alone and extending the overall detection range of the system.

Method 2000 begins at 2002 and includes receiving output from the primary signal detector and the secondary signal detector. A controller may receive respective signals (e.g., voltage signals) from the primary signal detector and the secondary signal detector corresponding to respective intensities of light measured at each detector.

At 2004, it is determined if the primary signal detector is below a threshold, for example, the saturation point of the detector. The saturation point refers to a voltage output above which increases in light intensity do not increase (or, alternatively, do not linearly increase) the voltage output of the detector. If the primary signal detector is below the threshold, method 2000 proceeds to 2006 and includes determining a sample transmittance signal based on output from the primary signal detector. Determining the sample transmittance signal may further include applying a reference correction based on output of the reference detector (if included) or the secondary detector, as indicated at 2007. Determining the sample transmittance signal based on output from the primary signal detector (and the reference correction based on output from the reference detector or secondary signal detector) may refer to a first mode of UV-VIS detector unit operation. Determining the sample transmittance signal and applying the reference correction are both described with respect to FIG. 17.

At 2010, method 2000 includes determining an absorbance of the sample based on the sample transmittance signal. For example, the controller may perform a blank correction on the sample transmittance signal, as described with respect to FIG. 2, to determine a light transmittance of the sample alone (without solvent) and may further convert the light transmittance to an absorbance value (e.g., according to $A=-\log_{10}T$), which may then be plotted against time (and/or fraction number) on the chromatogram. From the absorbance, a concentration of the sample may also be determined using the Beer-Lambert relationship. Following 2010, method 2000 ends.

Returning to 2004, if it is determined that the primary signal detector is not below the threshold, method 2000 proceeds to 2008 and includes determining the sample transmittance signal based on output from the secondary signal detector. Determining the sample transmittance signal may further include applying a reference correction based on output of the reference detector (if included), as indicated at 2009. Determining the sample transmittance signal based on output from the secondary signal detector (and the reference correction based on output from the reference detector) may refer to a second mode of UV-VIS detector unit operation. The method may then proceed to 2010, as described above. In configurations where a dedicated reference detector is not included, the sample measurement obtained by the secondary signal detector may be corrected using a pre-determined correction stored in a memory of the controller derived from characteristic curves of light source temperature, drive current, and/or drive voltage (such as the characteristic curves shown in FIGS. 26-27, for example).

In an alternative example, wherein the UV-VIS detector unit includes a primary signal detector, a secondary signal detector, and a dedicated reference detector (such as UV-VIS detector unit 1200 of FIG. 12), the sample absorbance (and thereby, concentration) may be determined as a weighted average of a first sample absorbance determined using output from the primary signal detector and a second sample absorbance determined using output from the secondary signal detector. For example, the closer the primary signal detector becomes to its saturation point, the less relative weight the first sample absorbance is given (e.g., down to 0% when the primary signal detector is at its saturation point).

If the sample contains fluorescent analytes, it may be further beneficial to include fluorescence detection. As fluorescence is more sensitive than absorbance, fluorescence measurements may enable lower concentrations of analyte to be detected than absorbance. Further, fluorescence may provide additional information as to the identity of an unknown compound. Fluorescence and absorbance may be measured simultaneously using a beam splitter and a second, dedicated fluorescence detector (e.g., as shown for UV-VIS detector unit 1300 of FIG. 13), such as according to an example method 2100 of FIG. 21, or synchronously, such as according to an example method 2200 of FIG. 22. Notably, both fluorescence and absorbance measurements may be performed using a single light source (e.g., first light source 1310 of FIG. 13).

Figure 21:
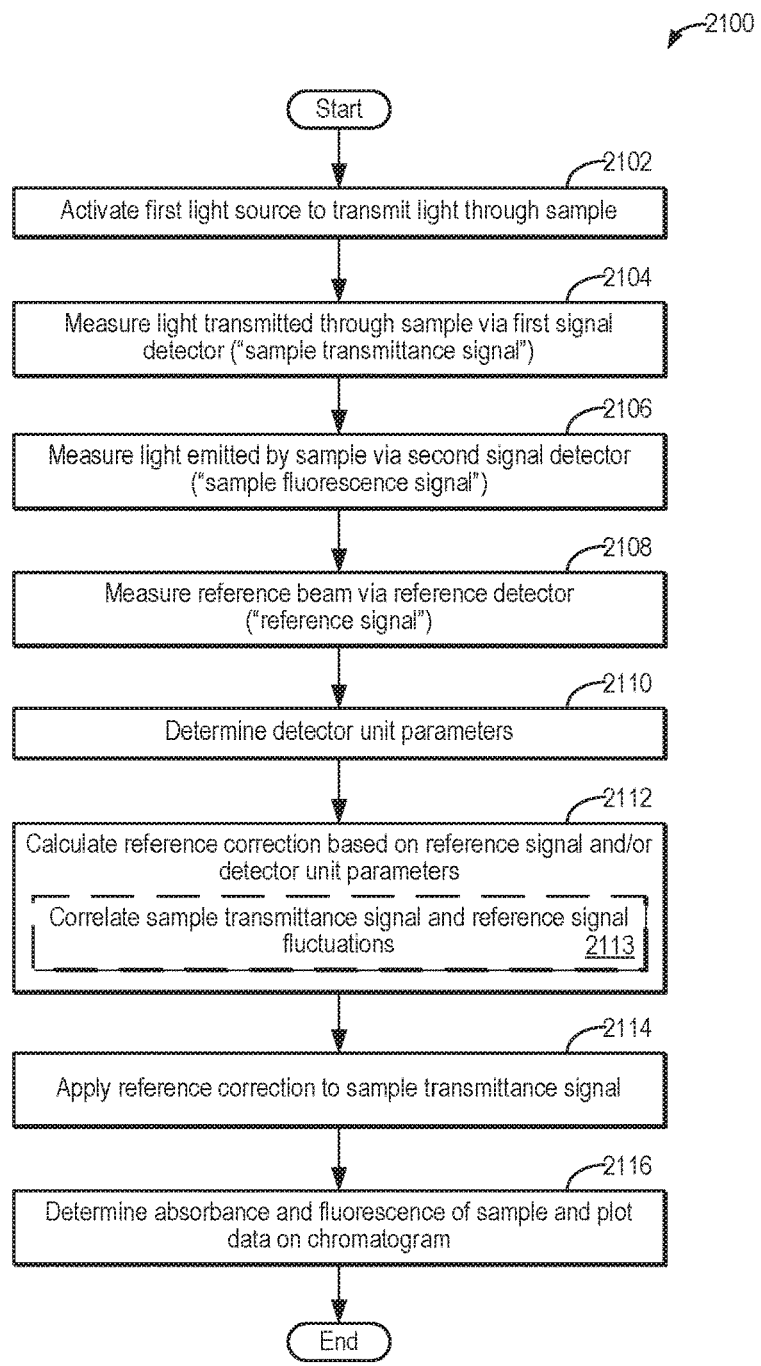
FIG. 21 illustrates an example method for performing simultaneous absorbance and fluorescence measurements using a UV-VIS detector unit.

Turning first to FIG. 21, method 2100 begins at 2102 and includes activating the first light source to transmit light through the sample. In some examples, the UV-VIS detector may include one light source, and thus, the first light source is the only light source of the UV-VIS detector unit. In other examples, the UV-VIS detector may include multiple light sources, and the first light source is a light source that shares a common axis with a flow path for interrogating the sample within a flow cell. In both examples, the first light source may include one or more emitters, which may be controlled according to method 1800 of FIG. 18, for example. The first light source may be activated at a predetermined duty cycle and drive current to emit a desired light intensity.

At 2104, method 2100 includes measuring the light transmitted through the sample via the first signal detector. The corresponding signal output by the first signal detector may be referred to as a "sample transmittance signal," which is received by a controller (e.g., the controller of control system 110 of FIG. 1) and which may be converted to a "sample absorbance signal," as described further below.

At 2106, method 2100 includes measuring light emitted by the sample via the second signal detector. The corresponding signal output by the second signal detector may be referred to as a "sample fluorescence signal," which is received by the controller.

At 2108, method 2100 includes measuring the reference beam via a reference detector. The reference beam may be generated by a second light source or by the first light source (e.g., using a beam splitter, a reflector, or coupling optics), depending on the UV-VIS detector unit configuration. The reference beam includes light that has not been transmitted through the sample. The reference detector may output a signal to the controller relative to the intensity of light measured by the reference detector, which may be referred to as a "reference signal."

At 2110, method 2000 includes determining detector unit parameters. Detector unit parameters may include the intensity of the light source(s), a temperature at a location of interest, an electrical current driving the light source(s), an electrical voltage across the light source(s), etc. The location of interest may be near the light source(s), at a flow cell, near the signal detector, or at a thermal device coupled to the light source(s), for example. The intensity the light source(s) may be determined based on the measured parameters (e.g., electrical drive current, drive voltage, pulse width of activation, and temperature) and known characteristics of the light source(s) (e.g., thermal structure functions, which describe the thermal dynamics of the system, thermal mass, and thermal resistance) or may be directly measured. Other parameters, such as light source output wavelength, may also be controlled (e.g., by modulating the temperature of the light source, such as illustrated in FIG. 28).

At 2112, method 2100 includes calculating a reference correction based on the reference signal and/or detector unit parameters, as described with respect to FIG. 17 (e.g., at 1714). Method 2100 may optionally further include correlating the sample transmittance signal and reference signal fluctuations, as indicated at 2113 and as further described with respect to FIG. 17 (e.g., at 1715).

At 2114, method 2100 includes applying the reference correction to the sample transmittance signal. For example, an intensity of transmitted light measured by the signal detector at time t, $I_{SIG(t)}$ may be transformed into a corrected intensity $I_{SIG(t)}*$ according to: $I_{SIG(t)}* = C_t \times I_{SIG(t)}$. In this way, data may be corrected for each time point individually.

At 2116, method 2100 includes determining the absorbance and the fluorescence of the sample and plotting data on a chromatogram. For example, the controller may perform a blank correction on the corrected sample transmittance signal, as described with respect to FIG. 2, to determine a light transmittance of the sample alone (without solvent) and may further convert the light transmittance to an absorbance value, which may then be plotted against time (and/or fraction number) on the chromatogram. At a given measurement time, the sample may contain no analytes (if only solvent is present) or a plurality of analytes. However, if the sample contains one analyte that is known, the concentration of the analyte may also be determined according to the Beer-Lambert law. In other examples, the concentration of total analyte present may be approximated using the absorbance of the sample and the Beer-Lambert relationship. The controller may also perform a blank correction on the sample fluorescence signal in a similar manner, using the fluorescence signal measured when no analytes were present. The fluorescence of the sample may be determined directly from the sample fluorescence signal and shown as relative fluorescence intensity (or other arbitrary units). The sample fluorescence may be overlaid on the same chromatogram as the sample absorbance or plotted on a separated chromatogram. Following 2116, method 2100 ends.

Figure 22:
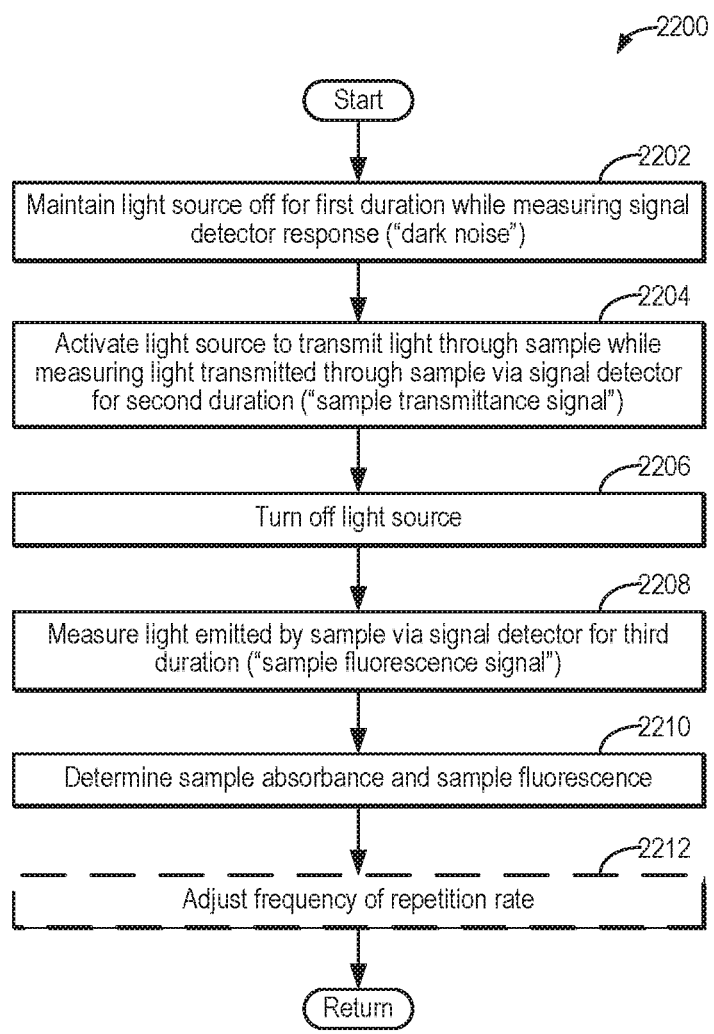
FIG. 22 illustrates an example method for performing synchronous absorbance and fluorescence measurements using a UV-VIS detector unit.

Turning next to FIG. 22, example method 2200 shows how both sample absorbance and fluorescence may be determined using a single signal detector. Method 2200 begins at 2202 and includes maintaining the light source off for a first duration while measuring the signal detector response. The signal detector response measured during the first duration may be referred to as "dark noise." Dark noise may be a relatively small electric current that flows through the signal detector even when no light is entering the device. By measuring the dark noise, a controller may determine a baseline of the signal detector, which may enable small changes in fluorescence to be sensitively measured. For example, the dark noise may establish a lower limit of a measurement signal (e.g., the measurement signal cannot be below the dark noise) and may further establish a limit of detection (LOD) and a limit of quantification (LOQ). The LOD may be defined as the lowest quantity or concentration of a component that can be detected with reasonable certainty, corresponding to a signal with a predefined margin above the dark noise (e.g., 3× the dark noise level). It ensures no overlap between statistical distributions of the dark noise and the detected analyte signal. The LOQ is more stringent than the LOD (e.g., 10× the dark noise level), defining the limit at which it can be confidently determined that two samples of analyte differ in concentration.

At 2204, method 2200 includes activating the light source to transmit light through the sample while measuring the light transmitted through the sample via the signal detector for a second duration. The signal detector response measured during the second duration may be referred to as a "sample transmittance signal," corresponding to the output of the signal detector received by the controller during the second duration.

At 2206, method 2200 includes turning off the light source. Turning off (e.g., deactivating) the light source may include stopping the power supplied to the light source, for example, or any other method of suitably interrupting the optical signal, such as shutters, irises, etc.

At 2208, method 2200 includes measuring light emitted by the sample via the signal detector for a third duration. The signal detector response measured during the third duration may be referred to as a "sample fluorescence signal," corresponding to the voltage output of the signal detector received by the controller during the third duration.

At 2210, method 2200 includes determining sample absorbance and sample fluorescence. The sample absorbance may be determined from the sample transmittance signal, which may be optionally corrected based on a reference signal and/or blank corrected, according to $A=-\log_{10}T$. The sample absorbance may be further used to determine sample concentration according to the Beer-Lambert relationship. The sample fluorescence may be reported as relative fluorescence intensity (or other arbitrary units). Both sample absorbance and sample fluorescence may be plotted on one or more chromatograms against time and/or fraction number.

Figure 29:
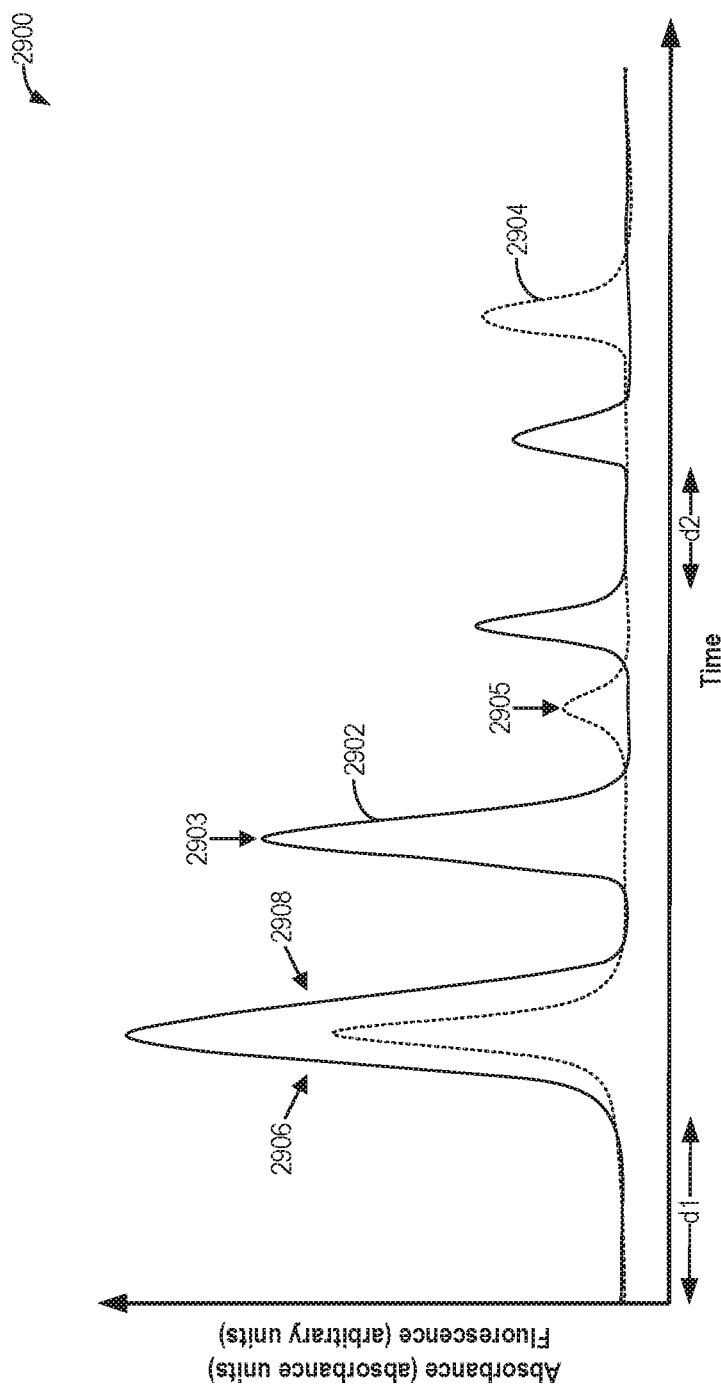
FIG. 29 depicts an example chromatogram with both sample absorbance and sample fluorescence plots.

For example, FIG. 29 shows an example chromatogram 2900 with both sample absorbance (plot 2902) and sample fluorescence (plot 2904) plotted against time (the X-axis). An example absorbance peak is indicated at 2903, and an example fluorescence peak is indicated at 2905. Each peak in the chromatogram indicates a presence of an analyte in the sample passing through the UV-VIS detector unit at the given time, with absorbance peaks corresponding to analytes that absorb light emitted by a light source and fluorescence peaks corresponding to analytes that absorb light emitted by a light source (which may be the same or different from the light source and/or wavelength of light used for the absorbance measurement) and re-emit it at a longer wavelength. As shown in the example of graph 2900, the absorbance and fluorescence peaks may overlap (as in the first set of peaks) or may be separate. Further, each peak has a leading edge, an example of which is indicated at 2906, and a trailing edge, an example of which is indicated at 2908. A duration d1 refers to a portion of the chromatogram before any peaks are detected, and a duration d2 refers to an example duration between detected peaks. During both d1 and d2 (and during other between peak durations), the sample may contain no analyte (e.g., only solvent), or the sample may contain analytes that are not detectable using the selected light source wavelength(s) and/or other UV-VIS detector unit settings (such as light source intensity, detector gain, etc.).

Returning to FIG. 22, at 2212, method 2200 optionally includes adjusting a frequency of a repetition rate. For example, a single measurement cycle may collectively comprise the first duration, the second duration (light source on time), and the third duration (light source off-time), and multiple measurement cycles may be performed with a fourth duration between each measurement cycle. Thus, adjusting the frequency of the repetition rate may include adjusting the length of the fourth duration. In another example, each duration may be varied (separately or in combination), such as by varying the on time vs. off time (traditionally known as pulse-width-modulation). Additionally, calculations from a previous cycle or dark current measurements may be performed during the second and third durations, or other combinations of interleaving techniques.

In one example, a burst data collection mode may be utilized in which ultra-high-speed sampling is used to extend the capability of UV-VIS detector unit electronics, such as by increasing both the analog-to-digital conversion and the sample collection capability (e.g., by collecting a greater number of sample signals within a given amount of time). The burst data collection mode may enable increased resolution of chromatography peak shapes and features at key points, such as the trailing edge (e.g., trailing edge 2908 of FIG. 29) or shoulder, and is particularly beneficial as chromatography speeds increase, such as in Ultra-High-Performance Liquid Chromatography (UHPLC). This also helps capture other very short time duration phenomena such as fluorescence lifetime, which can occur in the 1 picosecond time range after excitation, to be measured using this detector. This enables methods such as Fluorescence Lifetime Imaging (FLI) to be performed using the UV-VIS detector unit during a chromatography run in, for example, HPLC, UHPLC, or High-Performance Ion Chromatography (HPIC) systems.

As an example, the repetition rate may be adjusted in response to the absorbance or fluorescence characteristics of the analyte that is traversing the flow cell, allowing for a change in the sampling rate across a peak. For example, in response to a change in the second derivative of the signal from positive to negative as it crosses the inflection point of a peak, the repetition rate may be increased (the fourth duration is shortened). Then, as the second derivative of the signal switches from negative to positive, the repetition rate may be decreased (the fourth duration is lengthened). This type of control allows for increased sampling rate across peak maxima, which may be particularly beneficial for fluorescence-based measurements, increasing the signal-to-noise ratio. Additionally or alternatively, the UV-VIS detector unit could be configured with multiple fluorescence detectors, each with sensitivity optimized for the spectral fluorescence band(s), desired noise, and transient characteristics of the detector, or with suitable high speed capture circuitry.

As a second example, transient increases or decreases in sampling rate (as controlled by changes in the fourth duration) may allow for data compression of sections of a HPLC run in which no analyte is detected (e.g., the time between peaks, such as duration d2 shown in FIG. 29). Decreasing the sampling rate concentrates computing resources on relevant absorbance or fluorescence signals. This change in sampling rate may be triggered by one or more signals (fluorescence, absorbance, or both) crossing a respective threshold level for that signal type.

As a third example, for a mixed analyte containing multiple fluorescent components, multiple relevant emission wavelengths may be monitored. Measurement of each emission wavelength signal may be interleaved in separate measurement cycles. Appearance of a peak (as determined by threshold signal level, second derivative of the signal, etc.) at a specific emission wavelength may trigger a faster cycle (e.g., decrease the fourth duration) for the peak emission wavelength and increase the fourth duration for other cycles. Once the peak has passed, the cycles return to the starting interleaved condition. This may increase the signal-to-noise ratio and peak shape determination under conditions where multiple emission wavelengths are being monitored or where signal digitization (analog-to-digital conversion) or computing power is limited. Alternatively, multiple 8 bit measures of signals may be collected (including single or multiple fluorescence emission signals, single or multiple absorbance signals, single or multiple conductivity signals, or other measures). Then, in response to either a threshold, duration, or other triggering event being met, the relevant signal corresponding to the triggering event is selected and switched to 24 bit collection while the other (irrelevant) 8 bit signal measures are turned off.

As a fourth example, in preparative chromatography systems when large quantities of analyte are purified, monitoring for contaminants may be performed. The fourth duration may be decreased (e.g., the measurement cycle frequency is increased) both before a major peak emerges (e.g., during duration d1 of FIG. 29) and during its rise to a threshold level. Then, the fourth duration may be increased (e.g., the measurement cycle frequency is decreased) during the most concentrated part of the major peak. The fourth duration may be decreased again as the peak signal declines. This allows for data management limitations (for preparative systems) as typically, the concentration of the analyte during the most concentrated part of the major peak is higher than the detection range of the detector when looking at a direct signal (rather than a smaller quantity of the analyte split to a separate analytical flow cell). The over-range section of the peak may be of less interest than other sections of the preparative run, such as the leading and trailing edges where contaminant peaks may be located. Following 2212, method 2200 may return to begin the next measurement cycle.

Figure 30:
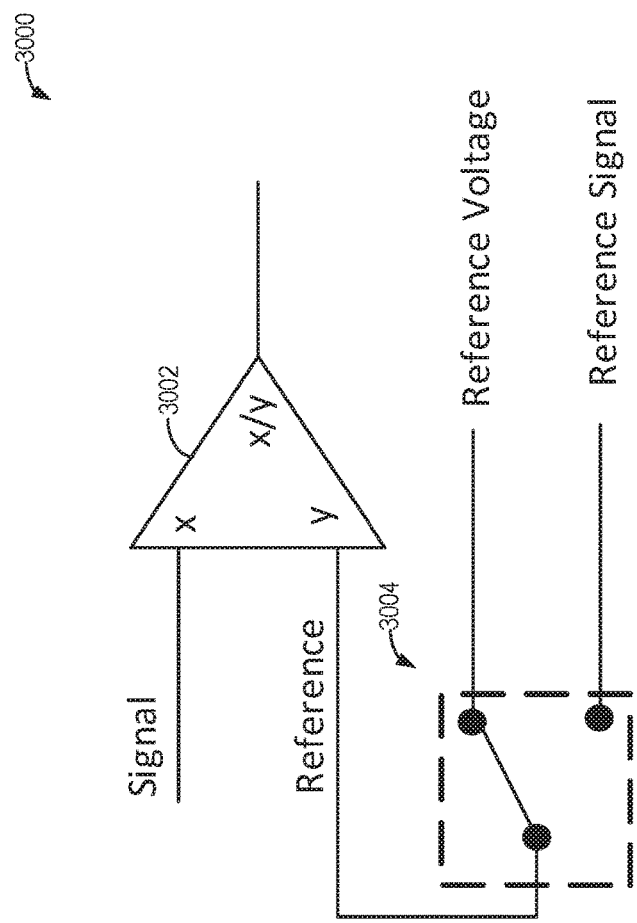
FIG. 30 depicts an example diagram of a ratiometric amplifier with a reference selector that may be used to adjust one or more parameters of a detector system.

FIG. 30 illustrates a diagram 3000 of a ratiometric amplifier/analog-to-digital converter with a reference selector that may be used to control light intensity output of a light source based on detector response. For example, the ratiometric amplifier/analog-to-digital converter with a reference selector may be used to perform the adjustments to the light intensity described above with respect to FIG. 19. As shown in diagram 3000, a ratiometric amplifier 3002 receives a signal input (x) and a reference input (y). The signal input may be received from a signal detector that is positioned to detect light that has passed through a flow path, and thus may reflect the level of absorbance of a sample. The reference input may be received from a reference detector, and thus may reflect a baseline level of light output from the light source. The ratiometric amplifier 3002 may output a ratio signal (x/y) that represents a ratio between the signal input and the reference input, e.g., the signal divided by the reference. In this way, the signal input may be normalized with respect to the reference value. The ratio signal may be used to control the light intensity of the light source. For example, the ratio signal may be used to adjust the electrical current supplied to the light source or to adjust the voltage across the light source.

In some examples, a reference selector 3004 may be present to select an appropriate reference signal. As shown, the reference selector 3004 may select between a reference voltage and the reference signal (where the reference signal is the signal output by the reference detector). The reference voltage may be a voltage supplied to the reference light source, a predetermined stored voltage, or other suitable voltage. The reference selector may be adjusted to couple a suitable reference to the amplifier. For example, the reference selector may toggle between the reference voltage and reference signal. In this way, the absorbance may be obtained directly in an analog circuit using a ratiometric amplifier/analog-to-digital converter. This may allow the system to minimize quantization errors and reduce or eliminate erroneous changes in light levels.

Other mechanisms for modulating light source output are possible. For example, the light source output may be varied at a frequency and measured using a lock-in amplifier. In another example, the flow rate of the solvent may be increased or reduced, potentially allowing interpolation below the analog-to-digital converter's resolution. Additionally or alternatively, another detector system may be placed upstream of the primary detector to allow a look-ahead or gain scheduling.

The diagram 3000 illustrates a mechanism to control the output level of the primary (signal) light source, but such a mechanism could additionally or alternatively be used to control a secondary (reference) light source. Other mechanisms for controlling light intensity may include a temperature taken at a location of interest, (e.g., near signal or source detectors, flow cell block, heat sink, etc.), which may be used for monitoring or controlling certain aspects of the system (e.g., light intensity, detector output). In some examples, electrical current driving the primary light source(s) or the reference light source(s) may be adjusted, while in other examples, electrical voltage across the primary light source(s) or the reference light source(s) may be adjusted. These adjustments may be made to match the dynamic response of the detector, the light source, the analog-to-digital converter, amplifiers, and other components in the systems.

Other analog control mechanisms may include automatic power control (APC), automatic gain control (AGC), and automatic current control (ACC) circuits. Such circuits may utilize open-loop or closed-loop feedback control. For example, an APC circuit may include closed-loop feedback control where a commanded voltage input is biased based on a negative feedback loop that includes a temperature-sensing device (e.g., thermistor). The output from the amplifier may include an irradiance or intensity control voltage that is supplied to a variable resistor that controls electrical current flow through the light source, for example.

The technical effect of including a secondary signal detector in a UV-VIS detector unit, wherein the secondary signal detector is configured to measure off-axis light that is back-reflected by a sample, is that smaller concentrations of the sample may be detected, increasing a detection range of the UV-VIS detector unit.

An example provides a system comprising a first light source; a signal detector; a flow path positioned intermediate the first light source and the signal detector, where the first light source, the signal detector, and the flow path are aligned along a first axis; a second light source; and a reference detector, the second light source and the reference detector aligned along a second axis, different than the first axis. In a first example of the system, the first and second light sources are mounted on a common substrate. In a second example of the system, which optionally includes the first example, the common substrate is coupled to a thermal control device. In a third example of the system, which optionally includes one or both of the first and second examples, the common substrate, the first light source, and the second light source are housed on a removable module, the removable module configured to be inserted and removed from a housing that houses the signal detector, the flow path, and the reference detector, and the signal detector, the flow path, and the reference detector are fixedly coupled to the housing. In a fourth example of the system, which optionally includes one or more or each of the first through third examples, the first light source is mounted to a first substrate and the second light source is mounted to a second substrate. In a fifth example of the system, which optionally includes one or more or each of the first through fourth examples, the first and second substrates are each coupled to common thermal control device. In a sixth example of the system, which optionally includes one or more or each of the first through fifth examples, the first substrate is coupled to first thermal control device and the second substrate is coupled to the second thermal control device. In a seventh example of the system, which optionally includes one or more or each of the first through sixth examples, the first thermal control device differs from the second thermal control device in at least one of size, thermal capacity, thermal conductivity, thermal diffusivity, and thermal mass. In an eighth example of the system, which optionally includes one or more or each of the first through seventh examples, the system further comprises a controller configured to correlate light intensity of the first light source to light intensity of the second light source. In a ninth example of the system, which optionally includes one or more or each of the first through eighth examples, the controller is further configured to: determine a sample transmittance signal based on output from the signal detector; determine a reference signal based on output from the reference detector; calculate a reference correction based on the reference signal and a correlation factor, the correlation factor correlating the light intensity of the first light source to the light intensity of the second light source; and calculate an absorbance of the sample based on the sample transmittance signal and the reference correction. In a tenth example of the system, which optionally includes one or more or each of the first through ninth examples, the system further comprises a temperature sensor configured to measure a temperature of the first light source and/or a temperature of the second light source. In an eleventh example of the system, which optionally includes one or more or each of the first through tenth examples, the first light source comprises more than one light emitter and/or the second light source comprises more than one light emitter. In a twelfth example of the system, which optionally includes one or more or each of the first through eleventh examples, the first light source and the second light source are electrically coupled in series. In a thirteenth example of the system, which optionally includes one or more or each of the first through twelfth examples, the first light source is configured to output light having a given wavelength range, and the second light source is configured to output light having the same given wavelength range.

Another example provides a system comprising a first light source and a second light source each mounted on a common substrate; a signal detector; a flow path positioned intermediate the first light source and the signal detector, where the first light source, the signal detector, and the flow path are aligned along a first axis; a reference detector, the second light source and the reference detector aligned along a second axis, different than the first axis; a thermal control device coupled to the common substrate; a temperature sensor coupled to the common substrate; and a controller configured to adjust the thermal control device based on output from the temperature sensor. In a first example of the system, the controller is configured to adjust the thermal control device to maintain the substrate within predetermined temperature range. In a second example of the system which optionally includes the first example, the controller is configured to: determine a sample transmittance signal based on output from the signal detector; determine a reference signal based on output from the reference detector; and calculate an absorbance of the sample based on the sample transmittance signal and the reference signal.

Another example provides a system comprising a detector unit including: a signal detector; a flow path configured to flow a sample; and a reference detector, where the signal detector, the flow path, and the reference detector are each positioned in a housing of the detector unit; and a first light source and a second light source each mounted on removable module, and when the removable module is inserted into the housing of the detector unit, the first light source, the flow path, and the signal detector are aligned along a first axis, and the second light source and reference detector are aligned along a second axis. In a first example, the system further comprises a thermal control device coupled to the removable module. In a second example, which optionally includes the first example, the system further comprises a thermal control device positioned in the housing of the detector unit, the thermal control device configured to control a temperature of the first light source and the second light source when the removable module is inserted into the housing of the detector unit.

In another representation, a system comprises a first light source; a primary signal detector; a flow path positioned intermediate the first light source and the primary signal detector, where the first light source, the signal detector, and the flow path are aligned along a first axis; a second light source; a reference detector, the second light source and the reference detector aligned along a second axis, different than the first axis; and a secondary signal detector positioned intermediate the first light source and the flow path and off-axis from the first axis. In the preceding example, the system additionally or alternatively further comprises a controller configured to: during a first mode, determine a first sample transmittance signal based on output from the primary signal detector, and calculate a first absorbance of a first sample in the flow path based on the first sample transmittance signal; and during a second mode, determine a second sample transmittance signal based on output from the secondary signal detector, and calculate a second absorbance of a second sample in the flow path based on the second sample transmittance signal. In any or all of the preceding examples, additionally or alternatively, the first mode comprises the primary signal detector receiving light from the first light source at a level below a saturation point of the primary signal detector, and wherein the second mode comprises the primary signal detector receiving light from the first light source at a level above the saturation point of the primary signal detector. In any or all of the preceding examples, additionally or alternatively, during the first mode, the first absorbance is calculated based on the first sample transmittance signal without using any output from the secondary signal detector, and wherein during the second mode, the second absorbance is calculated based on the second sample transmittance signal without using any output from the primary signal detector. In any or all of the preceding examples, the controller is additionally or alternatively further configured to: during the first mode, determine a first reference signal based on output from the reference detector and correct the first absorbance based on the first reference signal; and during the second mode, determine a second reference signal based on output from the reference detector and correct the second absorbance based on the second reference signal. In any or all of the preceding examples, additionally or alternatively, the secondary signal detector is positioned off-axis from the second axis. In any or all of the preceding examples, additionally or alternatively, light emitted by the first light source that is detected by the primary signal detector travels from the first light source to the primary signal detector without passing through a beam splitter.

In another representation, a method comprises determining a first sample transmittance signal based on output from a primary signal detector positioned to receive light emitted by a light source and that has passed through a flow path; when the first sample transmittance signal is below a threshold value, calculating an absorbance of a sample in the flow path based on the first sample transmittance signal; and when the first sample transmittance signal is above the threshold value, calculating the absorbance of the sample in the flow path based on a second sample transmittance signal, the second sample transmittance signal determined based on output from a secondary detector positioned between the light source and the flow path. In the preceding example, additionally or alternatively, calculating the absorbance of the sample in the flow path based on the first sample transmittance signal comprises determining a first reference signal based on output from the secondary detector and calculating the absorbance of the sample in the flow path based on the first sample transmittance signal and the first reference signal. In any or all of the preceding examples, additionally or alternatively, calculating the absorbance of the sample in the flow path based on the first sample transmittance signal comprises determining a first reference signal based on output from a reference detector and calculating the absorbance of the sample in the flow path based on the first sample transmittance signal and the first reference signal, and calculating the absorbance of the sample in the flow path based on the second sample transmittance signal comprises determining a second reference signal based on output from the reference detector and calculating the absorbance of the sample in the flow path based on the second sample transmittance signal and the second reference signal. In any or all of the preceding examples, additionally or alternatively, calculating the absorbance of the sample in the flow path based on the second sample transmittance signal comprises calculating the absorbance of the sample in the flow path based on the second sample transmittance signal without correcting the absorbance based on a reference signal.

In another representation, a system comprises a light source; a primary signal detector; a flow path positioned intermediate the light source and the primary signal detector, where the light source, the primary signal detector, and the flow path are aligned along a common axis; coupling optics positioned intermediate the light source and the flow path; a secondary signal detector positioned intermediate the light source and the flow path and off-axis from the common axis; and a controller configured to: during a first mode, determine a first sample transmittance signal based on output from the primary signal detector, determine a reference signal based on output from the secondary signal detector, and calculate a first absorbance of a first sample in the flow path based on the first sample transmittance signal and the reference signal; and during a second mode, determine a second sample transmittance signal based on output from the secondary signal detector, and calculate a second absorbance of a second sample in the flow path based on the second sample transmittance signal. In the preceding example, additionally or alternatively, the first mode comprises the primary signal detector receiving light from the light source at a level below a saturation point of the primary signal detector, and the second mode comprises the primary signal detector receiving light from the light source at a level above the saturation point of the primary signal detector. In any or all of the preceding examples, additionally or alternatively, the coupling optics comprise a first coupling optic and a second coupling optic. In any or all of the preceding examples, additionally or alternatively, the reference detector is positioned between the first coupling optic and the second coupling optic. In any or all of the preceding examples, additionally or alternatively, the reference detector is positioned between the first coupling optic and the substrate. In any or all of the preceding examples, additionally or alternatively, light emitted by the light source that is detected by the primary signal detector travels from the light source to the primary signal detector without passing through a beam splitter. In any or all of the preceding examples, additionally or alternatively, during the second mode, the second absorbance is calculated based on the second sample transmittance signal without using any output from the primary signal detector. In any or all of the preceding examples, the controller is additionally or alternatively further configured to, during a third mode: determine a third sample transmittance signal based on output from the primary signal detector, determine a fourth sample transmittance signal based on output from the secondary signal detector; and calculate a third absorbance of a third sample in the flow path based on the third sample transmittance signal and the fourth sample transmittance signal, without correcting the third absorbance by a reference signal. In any or all of the preceding examples, additionally or alternatively, during the second mode, the second absorbance is calculated based on the second sample transmittance signal without correcting the second absorbance by a reference signal.

In another representation, a system includes a light source; a signal detector; a flow path positioned intermediate the light source and the signal detector; and a reference detector housed in a common housing with the light source. The reference detector is configured to detect light reflected from the housing and/or components within the housing. In a first example of the system, the components within the housing include coupling optics positioned intermediate the light source and the flow path. In a second example of the system, which optionally includes the first example, the coupling optics comprise a first lens and a second lens. In a third example of the system that optionally includes one or both of the first and second examples, the reference detector is positioned between the first lens and the second lens and is configured to detect light reflected from the first lens and the second lens. In a fourth example of the system, which optionally includes one or more or each of the first through third examples, the reference detector is positioned between the first lens and the light source and is configured to detect light reflected from the first lens. In a fifth example of the system, which optionally includes one or more or each of the first through fourth examples, the light source is mounted on a substrate and the reference detector is positioned on the substrate and is configured to detect light reflected from the first lens. In a sixth example of the system, which optionally includes one or more or each of the first through fourth examples, the light source, the flow path, and the signal detector are positioned along a common axis, and the reference detector is positioned off-axis from the common axis. In a seventh example of the system, which optionally includes one or more or each of the first through sixth examples, light emitted by the light source that is detected by the signal detector travels from the light source to the signal detector without passing through a beam splitter, and light reflected from the housing and/or components that is detected by the reference detector does not pass through a beam splitter. In an eighth example of the system, which optionally includes one or more or each of the first through seventh examples, the system further comprises a controller configured to: determine a sample transmittance signal based on output from the signal detector; determine a reference signal based on output from the reference detector; and calculate an absorbance of a sample in the flow path based on the sample transmittance signal and the reference signal.

In another representation, a system includes a light source mounted on a substrate; a signal detector; a flow path positioned intermediate the light source and the signal detector, where the light source, the signal detector, and the flow path are aligned along a common axis; a reference detector mounted on the substrate; and a reflector positioned to direct light from the light source to the reference detector, the reflector positioned off-axis from the common axis. In a first example of the system, the system further comprises coupling optics positioned intermediate the light source and flow path. In a second example of the system, which optionally includes the first example, the coupling optics are positioned intermediate the reflector and the flow path and are aligned along the common axis. In a third example of the system, which optionally includes one or both of the first and second examples, light emitted by the light source that is detected by the signal detector travels from the light source to the signal detector without passing through a beam splitter, and light reflected from the reflector that is detected by the reference detector does not pass through a beam splitter. In a fourth example of the system, which optionally includes one or more or each of the first through third examples, the system further comprises a controller configured to: determine a sample transmittance signal based on output from the signal detector; determine a reference signal based on output from the reference detector; and calculate an absorbance of a sample in the flow path based on the sample transmittance signal and the reference signal. In a fifth example of the system, which optionally includes one or more or each of the first through fourth examples, the system further comprises a thermal control device and a temperature sensor each mounted on the substrate, and the controller is further configured to adjust the thermal control device based on output from the temperature sensor.

In another representation, a system comprises a light source; a signal detector; a flow path positioned intermediate the light source and the signal detector, the flow path configured to flow a sample; coupling optics positioned intermediate the light source and the flow path; a reference detector positioned to detect light reflected from the coupling optics; and a controller configured to: determine a sample transmittance signal based on output from the signal detector; determine a reference signal based on output from the reference detector; and calculate an absorbance of the sample based on the sample transmittance signal and the reference signal. In a first example of the system, the flow path is configured to flow the sample along a longitudinal axis of the flow path, and wherein the flow path and light source are configured such that light emitted from the light source is transmitted through the flow path to the signal detector along the longitudinal axis. In a second example of the system, which optionally includes the first example, the coupling optics comprise a first lens and a second lens. In a third example of the system, which optionally includes one or both of the first and second examples, the reference detector is positioned between the first lens and the second lens and is configured to detect light reflected from the first lens and the second lens. In a fourth example of the system, which optionally includes one or more or each of the first through third examples, the reference detector is positioned between the first lens and the light source and is configured to detect light reflected from the first lens. In a fifth example of the system, which optionally includes one or more or each of the first through fourth examples, the light source is mounted on a substrate and the reference detector is positioned on the substrate and is configured to detect light reflected from the first lens.

In another representation, a method for a detector unit including a light source, a signal detector, and a flow path, comprises dynamically adjusting an intensity of light emitted by the light source based on one or more parameters of the detector unit; determining a sample transmittance signal based on output from the signal detector, the signal detector positioned to receive light emitted by the light source and passed through the flow path; and calculating an absorbance of a sample in the flow cell based on the sample transmittance signal. In a first example of the method, calculating the absorbance of the sample in the flow cell based on the sample transmittance signal comprises determining a reference transmittance signal based on output from a reference detector and calculating the absorbance of the sample in the flow cell based on the sample transmittance signal and the reference transmittance signal. In a second example of the method, which optionally includes the first example, the method further comprises applying a correction factor to the sample transmittance signal, the correction factor based on output from the signal detector when an analyte concentration of the sample in the flow cell is zero. In a third example of the method, which optionally includes one or both of the first and second examples, the light source is a first light source, and dynamically adjusting the intensity of the light emitted by the first light source based on one or more parameters of the detector unit comprises dynamically adjusting the intensity of the light emitted by the first light source based on an intensity of light emitted by a second light source, the second light source thermally and electrically coupled to the first light source and positioned off-axis from an axis of the flow path, the first light source, and the signal detector. In a fourth example of the method, which optionally includes one or more or each of the first through third examples, dynamically adjusting the intensity of the light emitted by the light source based on one or more parameters of the detector unit comprises dynamically adjusting the intensity of the light emitted by the light source based on a temperature of the light source. In a fifth example of the method, which optionally includes one or more or each of the first through fourth examples, dynamically adjusting the intensity of the light emitted by the light source based on one or more parameters of the detector unit comprises dynamically adjusting the intensity of the light emitted by the light source based on the intensity of the light source. In a sixth example of the method, which optionally includes one or more or each of the first through fifth examples, dynamically adjusting the intensity of the light emitted by the light source based on one or more parameters of the detector unit comprises dynamically adjusting the intensity of the light emitted by the light source based on the sample transmittance signal. In a seventh example of the method, which optionally includes one or more or each of the first through sixth examples, dynamically adjusting the intensity of the light emitted by the light source based on the sample transmittance signal comprises increasing the intensity of the light emitted by the light source as the sample transmittance signal decreases and decreasing the intensity of the light emitted by the light source as the sample transmittance signal increases. In an eighth example of the method, which optionally includes one or more or each of the first through seventh examples, dynamically adjusting the intensity of the light emitted by the light source based on one or more parameters of the detector unit comprises dynamically adjusting the intensity of the light emitted by the light source based on a calibration function. In a ninth example of the method, which optionally includes one or more or each of the first through eighth examples, dynamically adjusting the intensity of the light source comprises one or more of adjusting electrical drive current or voltage supplied to the light source, adjusting a temperature of the light source, and adjusting an amount of light reaching the flow path by adjusting a neutral density filter, a variable attenuator, or an adjustable aperture or iris.

In another representation, a method for a detector unit including a light source, a signal detector, and a flow path, comprises determining a sample transmittance signal based on output from the signal detector, the signal detector positioned to receive light emitted by the light source and passed through the flow path; calculating an absorbance of a sample in the flow cell based on the sample transmittance signal; and adjusting an intensity of light emitted by the light source responsive to the sample transmittance signal being greater than a threshold value. In a first example, adjusting the intensity of light emitted by the light source responsive to the sample transmittance signal being greater than the threshold value comprises reducing the intensity of light emitted by the light source responsive to the sample transmittance signal being greater than the threshold value. In a second example of the method, which optionally includes the first example, the threshold value is a first threshold value, and the method further comprises adjusting the intensity of light emitted by the light source responsive to the sample transmittance signal being less than a second threshold value that is lower than the first threshold value. In a third example of the method, which optionally includes one or both of the first and second examples, adjusting the intensity of light emitted by the light source responsive to the sample transmittance signal being less than the second threshold value comprises increasing the intensity of light emitted by the light source responsive to the sample transmittance signal being less than the second threshold value.

In another representation, a method for a detector unit including a light source, a signal detector, and a flow path, comprises determining a sample transmittance signal based on output from the signal detector, the signal detector positioned to receive light emitted by the light source and that has passed through the flow path; dynamically adjusting a response of the signal detector based on one or more of a temperature of the detector unit, a light intensity value, and the sample transmittance signal; and calculating an absorbance of a sample in the flow cell based on the sample transmittance signal. In a first example of the method, the light intensity value is a light intensity of the light source. In a second example of the method, which optionally includes the first example, the light intensity value is a light intensity of a second light source. In a third example of the method, which optionally includes one or both of the first and second examples, the method further comprises determining a reference transmittance signal based on output from a reference detector, the reference detector positioned to receive light emitted by the second light source, and wherein calculating the absorbance of the sample in the flow cell based on the sample transmittance signal comprises calculating the absorbance of the sample in the flow cell based on the sample transmittance signal and based on the reference transmittance signal. In a fourth example of the method, which optionally includes one or more or each of the first through third examples, the temperature of the detector unit comprises one or more of a temperature of the light source and a temperature of a substrate to which the light source is coupled. In a fifth example of the method, which optionally includes one or more or each of the first through fourth examples, dynamically adjusting the response of the signal detector based on the sample transmittance signal comprises increasing a detector gain as the sample transmittance signal decreases and reducing the detector gain as the sample transmittance signal increases.

In another representation, a system comprises a first light source; a first signal detector; a first flow path positioned intermediate the first light source and the first signal detector, where the first flow path, the first light source, and the signal detector are aligned along a first axis; a second signal detector; and a second flow path, where the second flow path and the second signal detector are aligned along a second axis, the first flow path fluidically coupled to the second flow path. In a first example, the system further comprises a second light source aligned along the second axis, the second flow path positioned intermediate the second light source and the second signal detector. In a second example of the system, which optionally includes the first example, the system further comprises a controller configured to determine a first sample transmittance signal based on output from the first signal detector, and calculate a first absorbance of a sample in the first flow path based on the first sample transmittance signal. In a third example of the system, which optionally includes one or both of the first and second examples, the controller is further configured to determine a second sample transmittance signal based on output from the second signal detector, and calculate a second absorbance of a sample in the second flow path based on the second sample transmittance signal. In a fourth example of the system, which optionally includes one or more or each of the first through third examples, the system further comprises a reference detector, and the controller is configured to: determine a reference signal based on output from the reference detector; calculate the first absorbance of the sample in the first flow path based on the first sample transmittance signal and further based on the reference signal; and calculate the second absorbance of the sample in the second flow path based on the second sample transmittance signal and further based on the reference signal. In a fifth example of the system, which optionally includes one or more or each of the first through fourth examples, the system further comprises coupling optics positioned intermediate the first light source and the first flow path, and the reference detector is positioned intermediate the coupling optics and the first light source.

In another representation, a light detector system comprises a light source comprising a plurality of light emitters; a signal detector; a flow path positioned intermediate the light source and the signal detector; and a controller configured to modulate one or more light emitters of the plurality of light emitters based on parameters of the light detector system. In a first example, the plurality of light emitters are arranged in an array, where each light emitter is positioned to emit light along at least a portion of the flow path. In a second example of the system, which optionally includes the first example, the plurality of light emitters arranged in the array comprises four light emitters arranged in a two by two array. In a third example of the system, which optionally includes one or both of the first and second examples, the flow path is configured to flow a sample along a longitudinal axis of the flow path, and the flow path and light source are configured such that light emitted from each light emitter is transmitted through the flow path along a respective axis parallel to the longitudinal axis. In a fourth example of the system, which optionally includes one or more or each of the first through third examples, the controller is configured to modulate one or more of the plurality of light emitters by: during a first mode, activating a first light emitter of the plurality of light emitters, maintaining a second light emitter of the plurality of light emitters deactivated, and determining a first sample transmittance signal based on output from the signal detector; and during a second mode, activating the second light emitter, maintaining the first light emitter deactivated, and determining a second sample transmittance signal based on output from the signal detector. In a fifth example of the system, which optionally includes one or more or each of the first through fourth examples, the controller is configured to modulate one or more of the plurality of light emitters by, during a third mode, alternately activating and deactivating a first light emitter of the plurality of light emitters and a second light emitter of the plurality of light emitters, and determining a third sample transmittance signal based on output from the signal detector. In a sixth example of the system, which optionally includes one or more or each of the first through fifth examples, the controller is configured to modulate one or more of the plurality of light emitters based on parameters of the light detector system by adjusting one or more of a frequency and pulse width of the one or more of the plurality of light emitters based on a respective efficiency of each of the plurality of light emitters. In a seventh example of the system, which optionally includes one or more or each of the first through sixth examples, the controller is configured to modulate one or more of the plurality of light emitters by simultaneously activating at least two light emitters of the plurality of light emitters.

In another representation, a system comprises a first light source; a first signal detector; a first flow path positioned intermediate the first light source and the first signal detector; a second light source; a second signal detector; a second flow path positioned intermediate the second light source and the second signal detector, the first flow path fluidically coupled to the second flow path; and a controller configured to: determine a first sample transmittance signal based on output from the first signal detector as a sample flows through the first flow path, and calculate a first absorbance of the sample based on the first sample transmittance signal; determine a second sample transmittance signal based on output from the second signal detector as the sample flows through the second flow path; and calculate a second absorbance of the sample based on the second sample transmittance signal. In a first example, the controller is further configured to determine a reference transmittance signal based on output from the first signal detector as the sample flows through the second flow path, and correct the second absorbance of the sample based on the reference transmittance signal. In a second example of the system, which optionally includes the first example, the reference transmittance signal is a first reference transmittance signal, and the controller is configured to determine a second reference transmittance signal based on output from the second signal detector as the sample flows through the first flow path, and correct the first absorbance of the sample based on the second reference transmittance signal.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

FIGS. 1-16 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system comprising:
a first light source;
a signal detector configured to receive light output by the first light source;
a flow path positioned intermediate the first light source and the signal detector, where the first light source, the signal detector, and the flow path are aligned along a first axis;
a second light source; and
a reference detector configured to receive light output by the second light source, the second light source and the reference detector aligned along a second axis, different than the first axis, where the light output by the second light source is not diverted to any sample.

2. The system of claim 1, wherein the first and second light sources are mounted on a common substrate, the second axis is parallel to the first axis, and no portion of the light output by the first light source is diverted to the reference detector.

3. The system of claim 2, wherein the common substrate is coupled to a thermal control device.

4. The system of claim 2, wherein the common substrate, the first light source, and the second light source are housed on a removable module, the removable module configured to be inserted and removed from a housing that houses the signal detector, the flow path, and the reference detector, and wherein the signal detector, the flow path, and the reference detector are fixedly coupled to the housing.

5. The system of claim 1, wherein the first light source is mounted to a first substrate and the second light source is mounted to a second substrate.

6. The system of claim 5, wherein the first and second substrates are each coupled to a common thermal control device.

7. The system of claim 5, wherein the first substrate is coupled to a first thermal control device and the second substrate is coupled to a second thermal control device.

8. The system of claim 7, wherein the first thermal control device differs from the second thermal control device in at least one of size, thermal capacity, thermal conductivity, thermal diffusivity, and thermal mass.

9. The system of claim 5, further comprising a controller configured to correlate light intensity of the light output by the first light source to light intensity of the light output by the second light source.

10. The system of claim 9, wherein the controller is further configured to:
determine a sample transmittance signal based on output from the signal detector;
determine a reference signal based on output from the reference detector;
calculate a reference correction based on the reference signal and a correlation factor, the correlation factor correlating fluctuations in the light intensity of the light output by the first light source to fluctuations in the light intensity of the light output by the second light source, the reference correction accounting for changes in the light intensity of the light output by the first light source over time; and
calculate an absorbance of a sample based on the sample transmittance signal and the reference correction.

11. The system of claim 1, further comprising a temperature sensor configured to measure a temperature of the first light source and/or a temperature of the second light source.

12. The system of claim 1, wherein the first light source comprises more than one light emitter and/or the second light source comprises more than one light emitter.

13. The system of claim 1, wherein the first light source and the second light source are electrically coupled in series.

14. The system of claim 1, wherein the first light source is configured to output light having a given wavelength range, and the second light source is configured to output light having the same given wavelength range.

15. A system comprising
a first light source and a second light source each mounted on a common substrate;
a signal detector;
a flow path positioned intermediate the first light source and the signal detector, where the first light source, the signal detector, and the flow path are aligned along a first axis;
a reference detector, the second light source and the reference detector aligned along a second axis, different than the first axis, without a beam splitter positioned in a light path between the second light source and the reference detector;
a thermal control device coupled to the common substrate;
a temperature sensor coupled to the common substrate; and
a controller configured to adjust the thermal control device based on output from the temperature sensor.

16. The system of claim 15, wherein the controller is configured to adjust the thermal control device to maintain the substrate within a predetermined temperature range.

17. The system of claim 15, wherein the controller is configured to:
determine a sample transmittance signal based on output from the signal detector;
determine a reference signal based on output from the reference detector; and
calculate an absorbance of a sample based on the sample transmittance signal and the reference signal.

18. A system comprising:
a detector unit including:
a signal detector;
a flow path configured to flow a sample; and
a reference detector, where the signal detector, the flow path, and the reference detector are each fixedly positioned in a housing of the detector unit; and
a first light source and a second light source each mounted on a removable module that is separate from the detector unit when not inserted into the housing of the detector unit, and, when the removable module is inserted into the housing of the detector unit, the first light source, the flow path, and the signal detector are aligned along a first axis, and the second light source and the reference detector are aligned along a second axis.

19. The system of claim 18, further comprising a thermal control device coupled to the removable module, and wherein, when the removable module is inserted into the housing of the detector unit, the first light source transmits light through the flow path when activated and the second light source transmits light that is isolated from the flow path when activated.

20. The system of claim 18, further comprising a thermal control device positioned in the housing of the detector unit, the thermal control device configured to control a temperature of the first light source and the second light source when the removable module is inserted into the housing of the detector unit.

* * * * *